(12) United States Patent
Liu

(10) Patent No.: US 10,351,613 B2
(45) Date of Patent: Jul. 16, 2019

(54) POLYPEPTIDE FOR INHIBITION OF TUMOR

(71) Applicant: G-Bio Pharma Tech Co., Ltd., Shanghai (CN)

(72) Inventor: Hongli Liu, Shanghai (CN)

(73) Assignee: G-Bio Pharma Tech Co., Ltd., Shanghai (CN)

( * ) Notice: Subject to any disclaimer, the term of this patent is extended or adjusted under 35 U.S.C. 154(b) by 0 days.

(21) Appl. No.: 15/746,978

(22) PCT Filed: Jul. 21, 2016

(86) PCT No.: PCT/CN2016/090800
§ 371 (c)(1),
(2) Date: Jan. 23, 2018

(87) PCT Pub. No.: WO2017/016430
PCT Pub. Date: Feb. 2, 2017

(65) Prior Publication Data
US 2019/0010201 A1    Jan. 10, 2019

(30) Foreign Application Priority Data
Jul. 27, 2015  (CN) .......................... 2015 1 0446747

(51) Int. Cl.
| | | |
|---|---|---|
| *C07K 14/575* | (2006.01) | |
| *A61K 38/39* | (2006.01) | |
| *C12N 15/63* | (2006.01) | |
| *C07K 14/78* | (2006.01) | |
| *A61P 35/00* | (2006.01) | |
| *A61K 31/555* | (2006.01) | |
| *A61K 33/24* | (2019.01) | |
| *A61K 38/04* | (2006.01) | |
| *A61K 38/16* | (2006.01) | |

(52) U.S. Cl.
CPC ............ *C07K 14/575* (2013.01); *A61K 38/39* (2013.01); *A61P 35/00* (2018.01); *C07K 14/78* (2013.01); *C12N 15/63* (2013.01); *A61K 31/555* (2013.01); *A61K 33/24* (2013.01); *A61K 38/04* (2013.01); *A61K 38/16* (2013.01); *A61K 2300/00* (2013.01)

(58) Field of Classification Search
CPC ....... C07K 14/575; A61K 38/39; C12N 15/63
See application file for complete search history.

(56) References Cited

U.S. PATENT DOCUMENTS

| | | | | |
|---|---|---|---|---|
| 5,854,205 A | * | 12/1998 | O'Reilly ................ | C07K 14/78 514/13.3 |
| 6,174,861 B1 | * | 1/2001 | O'Reilly ................ | C07K 14/78 514/13.3 |
| 2003/0087393 A1 | * | 5/2003 | O'Reilly ................ | C07K 14/78 435/69.4 |
| 2004/0091465 A1 | * | 5/2004 | Yim .................... | A61K 31/7024 424/94.1 |

FOREIGN PATENT DOCUMENTS

| | | |
|---|---|---|
| CN | 102924578 A | 2/2013 |
| WO | 2005021756 A1 | 3/2005 |

OTHER PUBLICATIONS

Torres et al., 2011, Structural analysis of the N-terminal fragment of the antiangiogenic protein endostatin: A molecular dynamics study, Proteins, 79(9): 2684-2692.*
International Search Report for PCT/CN2016/090800, dated Oct. 27, 2016, 8 pages.

* cited by examiner

*Primary Examiner* — Amber D Steele
(74) *Attorney, Agent, or Firm* — Quarles & Brady LLP

(57) ABSTRACT

The present invention provides peptides for inhibiting tumor, which are fragments of the N terminus of endostatin, having 45 or less amino acid residues, and which at least contain amino acid residues 1-20 of the N terminus, wherein amino acid residues at positions 2 to 18 of the N terminus of endostatin are shown in the disclosure, and the peptides optionally contain mutations at positions 17 and 20-22 as disclosed in the disclosure. The present invention also relates to the coding sequences of the peptides, expression vectors containing the coding sequence, pharmaceutical compositions comprising the peptide, and use of the peptide and pharmaceutical composition in the inhibition, prevention or treatment of tumor.

20 Claims, 20 Drawing Sheets
Specification includes a Sequence Listing.

POLYPEPTIDE FOR INHIBITION OF TUMOR

CROSS-REFERENCE TO RELATED APPLICATIONS

This application represents the U.S. national stage entry of International Application No. PCT/CN2016/090800 filed Jul. 21, 2016, which claims priority to Chinese Patent Application No. 201510446747.4 filed Jul. 27, 2015, the disclosure of which is incorporated herein by reference in its entirety and for all purposes.

TECHNICAL FIELD

The present invention belongs to the field of tumor treatment, specifically relating to polypeptides used for inhibiting or treating tumor, the amino acid sequences of which are fragments of 45 or less amino acid residues from the first amino acid residue of the N terminus of endostatin.

TECHNICAL BACKGROUND

Endostatin is an endogenous angiogenesis inhibitor isolated and purified from supernate of cultured mouse endothelioma (EOMA) by O'Reilly et al., in 1997. It is derived from the hydrolysate of type XVIII collagen, with a molecular weight of 20 kD. As demonstrated by experiments, endostatin inhibits blood vessel endothelium and tumor cells. Because of the difficulties such as renaturation of the recombinant endostatin, EntreMed Inc. (USA) gave up clinical research for the recombinant endostatin. And currently it is unable to prepare endostatin having a relatively high in vitro activity in large quantities.

In endostatin, the three histidines at positions 1, 3 and 11 at the N terminus and the Asp residue at position 76 together form a zinc ion binding site. Binding to zinc ion is crucial for the activity of endostatin. It is reported that the polypeptide from the N terminus of endostatin exhibits a certain activity in inhibiting vascular endothelial cell and tumor cell (Cancer Res. 2005; 65(9):3656-63; U.S. Pat. No. 7,524,811 B2). However, the experiments also show that the polypeptide containing amino acid residues 1-25 of the N terminus of the human endostatin could not significantly inhibit growth of tumor from human source implanted in mouse model. Activity of the endostatin-derived polypeptides is still needed to be improved.

SUMMARY OF INVENTION

A polypeptide is provided, which is a fragment of the N terminus of endostatin having 45 or less amino acid residues, and which contains at least amino acid residues 1 to 20 of the N terminus, wherein amino acid residue at positions 2 and 18 of the N terminus of endostatin are respectively selected from the combinations as shown below:

| Amino acid residue at position 2 | Amino acid residue at position 18 |
| --- | --- |
| A | M |
| R | I |
| N | K |
| D | E, M, T or Y |
| Q | A or H |
| E | S or V |
| H | A or S |
| L | R, E or S |
| K | V |
| M | L or W |
| F | T |
| P | C or V |
| T | N, G, K, M, F, S or T |
| W | C, E, I, K, S or Y |
| Y | R, H, W or V |
| V | D or S | optionally, amino acid residue at position 17 of the N terminus of endostatin is S, A, L, I or T; and/or amino acid residue at position 20 is S or T; and/or, amino acid residue at position 21 is S or T, if present, and/or amino acid residue at position 22 is G, A, L, I or V, if present; and preferably, the amino acid sequence of the endostatin is set forth in SEQ ID NO: 1.

In one embodiment, the polypeptide contains at least amino acid residues 1-22 of SEQ ID NO: 38 and amino acid residues at positions 2 and 18 are defined as mentioned above.

In one embodiment, the polypeptide contains at least amino acid residues 1-25 of SEQ ID NO: 38 and amino acid residues at positions 2 and 18 are defined as mentioned above.

In one embodiment, the polypeptide contains at least amino acid residues 1-22, preferably amino acid residues 1-25, of SEQ ID NO: 38, and amino acid residue at position 2 is T, amino acid residue at position 18 is N, G, K, M, F, S or T, and amino acid residues at positions 17, 20, 21 and 22 are defined as mentioned above.

In one embodiment, the polypeptide contains at least amino acid residues 1-22, preferably amino acid residues 1-25, of SEQ ID NO: 38, and amino acid residue at position 18 is N, amino acid residue at position 2 is T, and amino acid residues at positions 17, 20, 21 and 22 are defined as mentioned above.

In one embodiment, the polypeptide contains at least amino acid residues 1-22, preferably amino acid residues 1-25, of SEQ ID NO: 38, and amino acid residue at position 18 is S, amino acid residue at position 2 is E, H, L, T, W or V, and amino acid residues at positions 17, 20, 21 and 22 are defined as mentioned above.

In one embodiment, the amino acid sequence of the polypeptide is set forth in any of SEQ ID NO: 4, 5, 6, 7, 27-30, 39 and 41.

In one embodiment, the polypeptide consists of SEQ ID NO: 38, wherein amino acid residue at position 2 is T, amino acid residue at position 18 is N or S, and amino acid residues at positions 17, 20, 21 and 22 are defined as mentioned above.

In one embodiment, the polypeptide is selected from amino acid sequences consisting of amino acid residue 1 to residue 39, 38, 37, 36, 34, 33, 32, 31, 29, 28, 27 or 26 of SEQ ID NO: 4, and amino acid sequences consisting of amino acid residue 1 to amino acid residue 39, 38, 37, 36, 35, 34, 33, 32, 31, 29, 28, 27, 26 or 25 of SEQ ID NO: 39.

In one embodiment, the first amino acid residue in the N terminus of the polypeptide is histidine, which is modified by formylation, acetylation, propionylation or butyrylation, and the first amino acid in the C terminus may be modified by PEG, cholesterol or amidation.

In one embodiment, the polypeptide is selected from the group consisting of:

HTHRDFQPVLHLVALNSSLSGGMRGIRGAD;

Ac-HTHRDFQPVLHLVALNSSLSGGMRGIRGAD;

HTHRDFQPVLHLVALNSSLSGGMRGIRGAD-NH$_2$;

Ac-HTHRDFQPVLHLVALNSSLSGGMRGIRGAD-NH$_2$;

Ac-HTHRDFQPVLHLVALNSSLSGGMRG-NH$_2$;

Ac-HTHRDFQPVLHLVALNSSLSGGMRGIRGADFQCFQ-NH$_2$;

Ac-HTHRDFQPVLHLVALNSSLSGGMRGIRGADFQCFQQARAV-NH$_2$;

HTHRDFQPVLHLVALNSNLSGGMRGIRGAD;

Ac-HTHRDFQPVLHLVALNSNLSGGMRGIRGAD;

HTHRDFQPVLHLVALNSNLSGGMRGIRGAD-NH$_2$;

Ac-HTHRDFQPVLHLVALNSNLSGGMRGIRGAD-NH$_2$;

Ac-HTHRDFQPVLHLVALNASLSGGMRGIRGAD-NH$_2$;

Ac-HTHRDFQPVLHLVALNSSLTGGMRGIRGAD-NH$_2$;

Ac-HTHRDFQPVLHLVALNASLTGGMRGIRGAD-NH$_2$; and

Ac-HTHRDFQPVLHLVALNSSLSGGMRGIRGA-NH$_2$;

wherein Ac represents acetylation modification and NH$_2$ represents amidation modification.

A polynucleotide sequence is provided, which is selected from the group consisting of:

(1) polynucleotide sequences encoding the polypeptides of the present disclosure; and (2) sequences complementary to any of the polynucleotide sequences of (1).

In one embodiment, the polynucleotide is selected from the group consisting of SEQ ID NO: 32, 33, 34, 35, 37 and 40.

In one embodiment, the polynucleotide is selected from polynucleotides consisting of base 1 to base 117, 114, 111, 108, 102, 99, 96, 93, 87, 84, 81 or 78 of SEQ ID NO: 32.

In one embodiment, the polynucleotide is selected from polynucleotides consisting of base 1 to base 117, 114, 111, 108, 105, 102, 99, 96, 93, 87, 84, 81, 78 or 75 of SEQ ID NO: 40.

An expression vector is provided in the present disclosure, which contains the polynucleotide of the present disclosure.

A pharmaceutical composition is provided in the present disclosure, which comprises the polypeptide of the present disclosure and a pharmaceutically acceptable carrier.

Use of the polypeptide or the pharmaceutical composition of the present disclosure in the preparation of a medicament for prevention or treatment of tumor is provided.

In one embodiment, the tumor is selected from the group consisting of lung carcinoma, lung squamous cell carcinoma, liver cancer, color cancer, pancreatic cancer, rhabdomyosarcoma, retinoblastoma, Ewing sarcoma, neuroblastoma and osteosarcoma.

Use of the polypeptide or the pharmaceutical composition of the present disclosure in the preparation of a medicament for improving the efficacy of a chemotherapy agent is provided.

In one embodiment, the chemotherapy agent is cisplatin, carboplatin or oxaliplatin.

A method for preparing the amino acid sequence of the present disclosure is provided, which comprises synthesizing the amino acid sequence by Fmoc solid phase synthesis.

BRIEF DESCRIPTION OF THE DRAWINGS

In FIG. 5a, curves, from top to bottom, as exemplified at the 2.5 mg/ml concentration, respectively indicates cell survival rates of P2S18, Endostar, Endostatin, P2T2, P2N18, P2, P2T2N18 and P2T2S18 (curves for P2T2N18 and P2T2S18 are partially overlapped). In FIG. 5b, curves, from top to bottom, as exemplified at the 2.5 mg/ml concentration, respectively indicates cell survival rates of Endostar, P2S18, Endostatin, P2T2, P2N18, P2, P2T2N18 and P2T2S18.

In FIGS. 11a and 11b, curves from top to bottom, as exemplified by the data at day 21, respectively indicate tumor volume (TV) and relative tumor volume (RTV) for negative control, endostar, P2, endostatin, positive control and P2T2S18.

In FIGS. 12a and 12b, curves from top to bottom, as exemplified by the data at day 21, respectively indicate tumor volume (TV) and relative tumor volume (RTV) for negative control, DDP (2 mg/kg), endostar+DDP, P2+DDP, endostatin+DDP, DDP (6 mg/kg) and P2T2S18+DDP.

SPECIFIC MODE FOR CARRYING OUT THE INVENTION

Figure 1A:
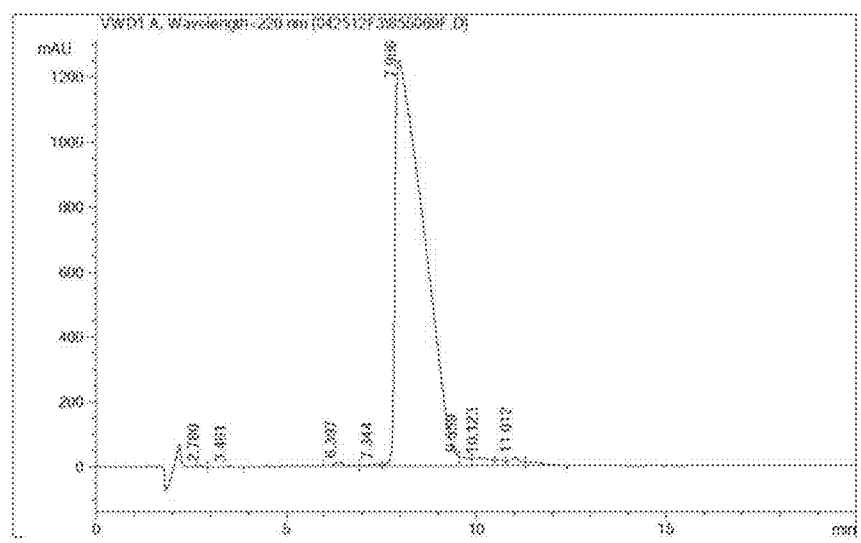
FIGS. 1a and 1b illustrate the HPLC and MASS maps of polypeptide P1, respectively.
Figure 1B:
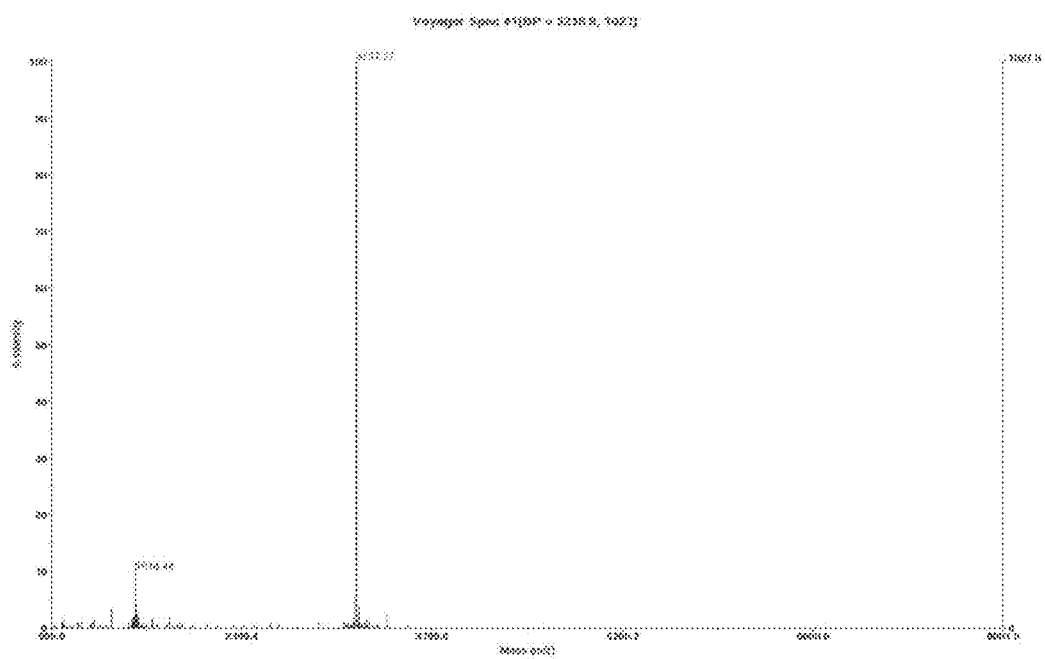
Figure 1C:
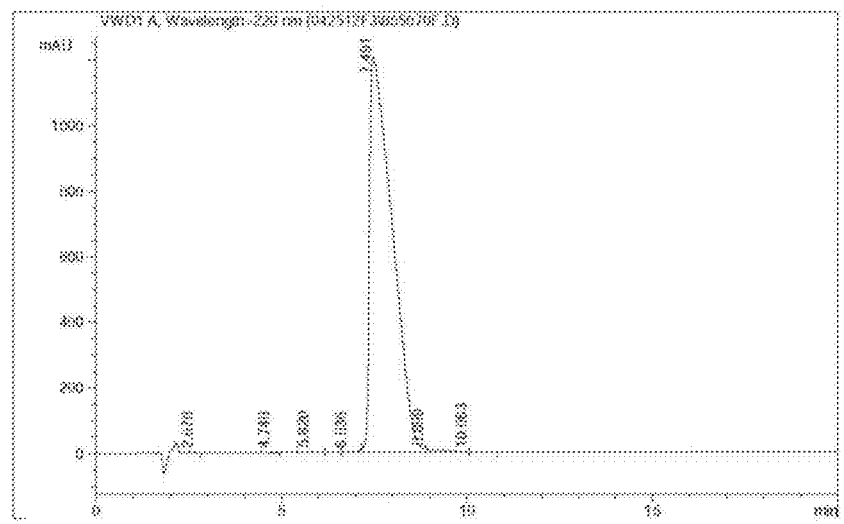
FIGS. 1c and 1d illustrate the HPLC and MASS maps of polypeptide P2, respectively.
Figure 1D:
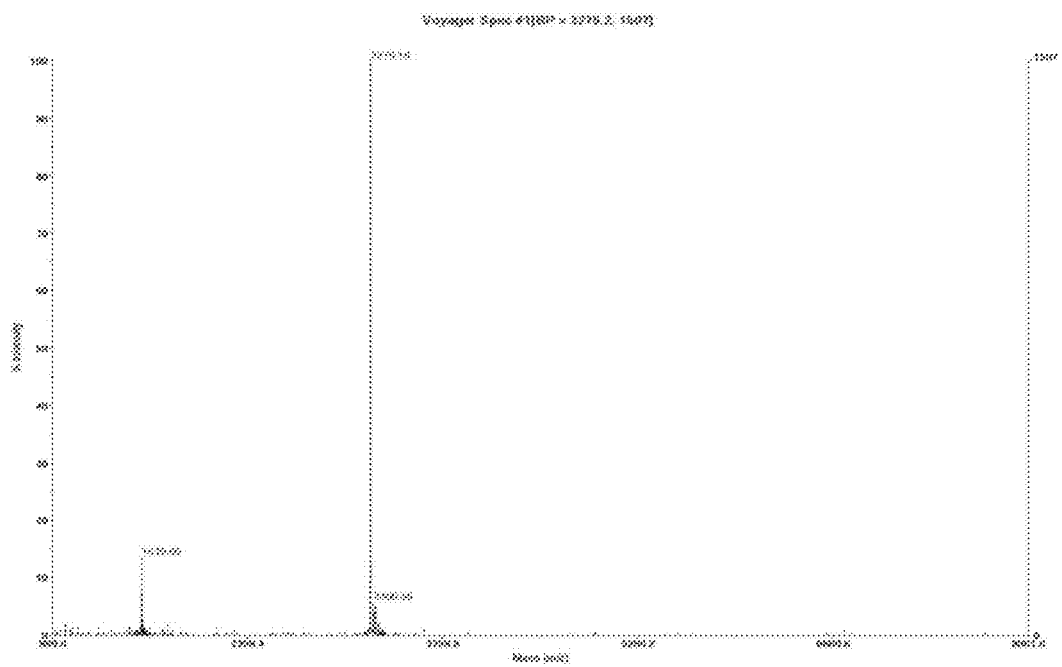
Figure 1E:
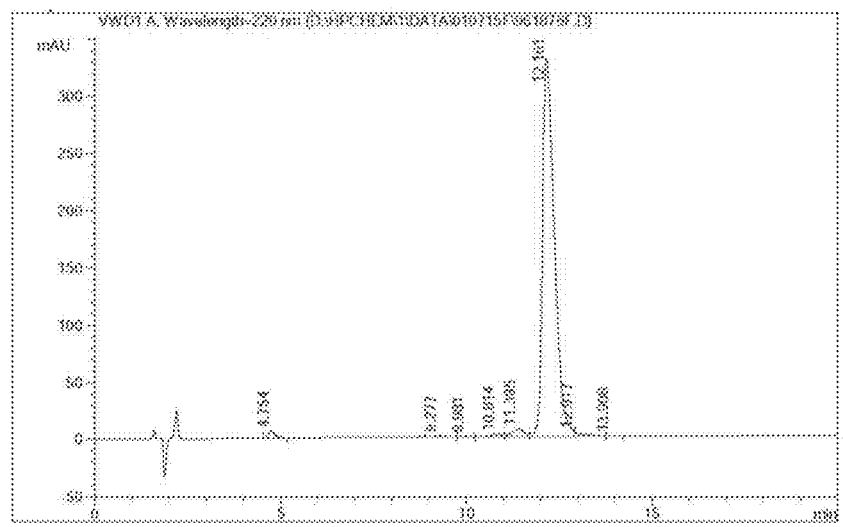
FIGS. 1e and 1f illustrate the HPLC and MASS maps of polypeptide P2T2S18, respectively.
Figure 1F:
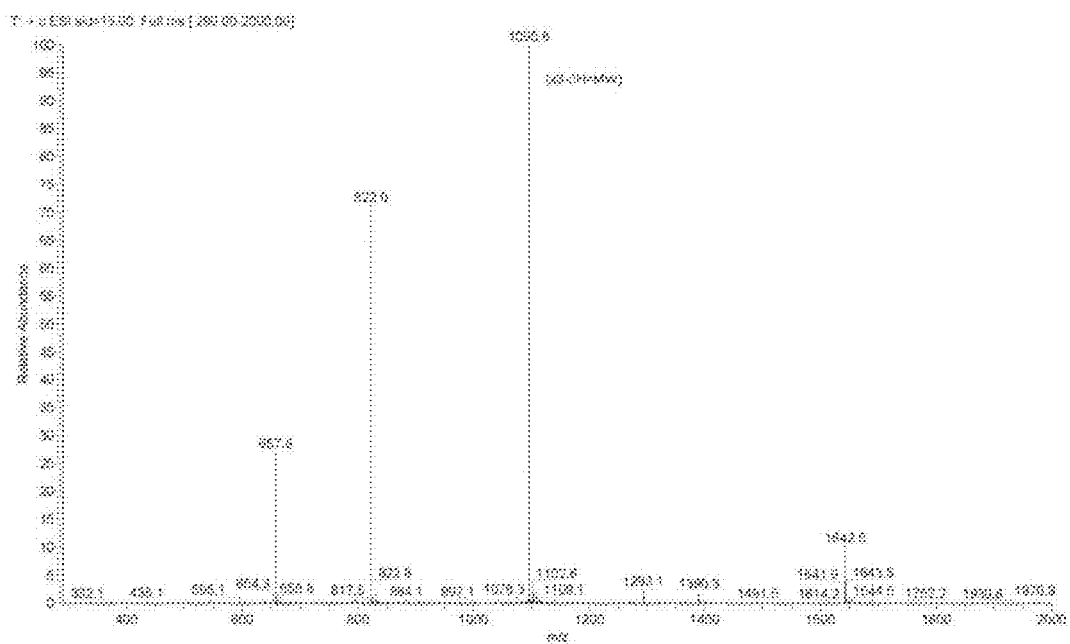
Figure 1G:
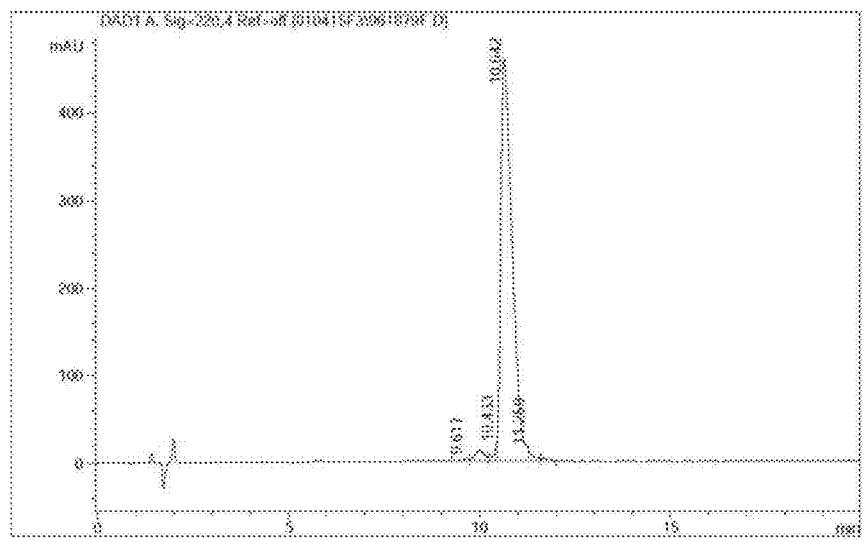
FIGS. 1g and 1h illustrate the HPLC and MASS maps of polypeptide P2T2N18, respectively.
Figure 1H:
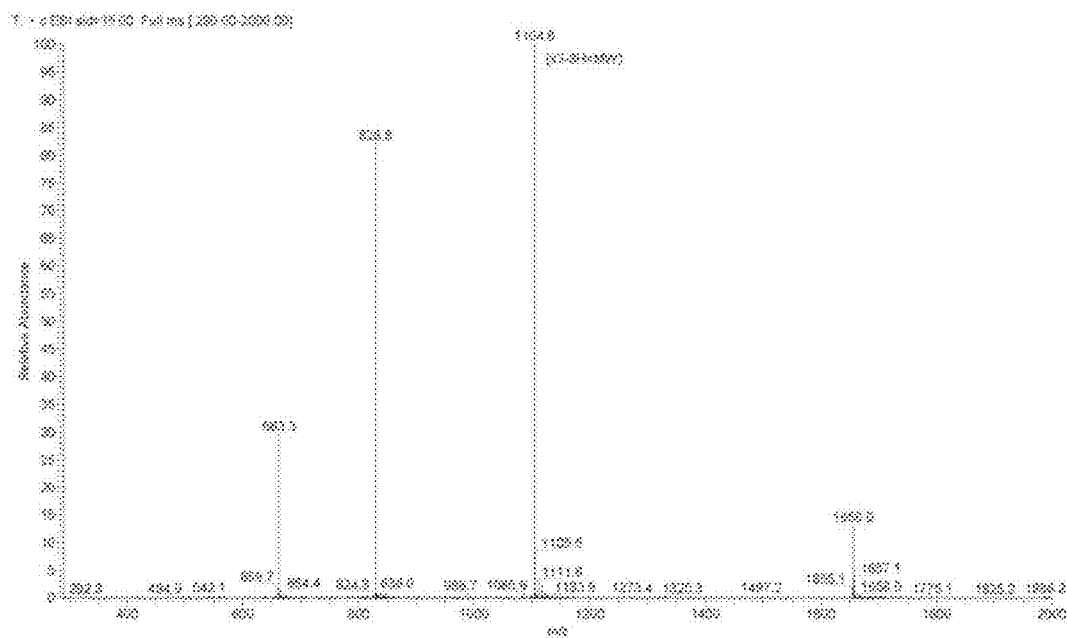

The polypeptide of the subject disclosure is a fragment of 45 or less amino acid residues of the N terminus of endostatin, which contains at least amino acid residues 1-20 of the N terminus of endostatin, and wherein:

(1) the residue corresponding to amino acid at position 2 (amino acid residue at position 2) of endostatin is A, R, N, D, Q, E, H, I, L, K, M, F, P, T, W, Y or V; and (2) the residue corresponding to amino acid at position 18 (amino acid residue at position 18) of endostatin is A, R, N, D, C, E, G, H, I, L, K, M, F, S, T, W, Y or V; and the inhibition rate of the polypeptide is higher than that of the corresponding polypeptide without mutation by at least 15%, preferably by at least 20%; or the $IC_{50}$ of the polypeptide is 50%, preferably 20%, more preferably 10%, of the $IC_{50}$ of the corresponding polypeptide without mutation.

Endostatin preferably is human endostatin. SEQ ID NO: 1 shows an example of the recombinant human vascular endostatin. Preferably, the amino acid sequences of the present disclosure contain at least amino acid residues 1-20 of the N terminus of the endostatin set forth in SEQ ID NO: 1 and the amino acid residues at positions 2 and 18 are defined as mentioned above.

Preferably, the residue of the polypeptide corresponding to the amino acid at position 2 of the N terminus of endostatin is D, L, T, W or Y. Preferably, the residue of the polypeptide corresponding to the amino acid at position 18 of the N terminus of endostatin is N, E, K, M, S, T or V. More preferably, the residue of the polypeptide corresponding to the amino acid at position 2 of the N terminus of endostatin is D, T, W or Y. More preferably, the residue of the polypeptide corresponding to the amino acid at position 18 of the N terminus of endostatin is N, S or V.

In some embodiments, the amino acid residues of the polypeptide corresponding to the amino acid at positions 2 and 18 of endostatin, respectively, are selected from the following combinations:

| Amino acid residue at position 2 | Amino acid residue at position 18 |
|---|---|
| A | M |
| R | I |
| N | K |
| D | E, M, T or Y |
| Q | A or H |
| E | S or V |
| H | A or S |
| L | R, E or S |
| K | V |
| M | L or W |
| F | T |
| P | C or V |
| T | N, G, K, M, F, S or T |
| W | C, E, I, K, S or Y |
| Y | R, H, W or V |
| V | D or S |

In some embodiments, the amino acid residues of the polypeptide corresponding to the amino acid at positions 2 and 18 of endostatin, respectively, are selected from the following combinations:

| Amino acid residue at position 2 | Amino acid residue at position 18 |
|---|---|
| A | M |
| R | I |
| N | K |
| D | E, M, T or Y |
| Q | A or H |
| E | S or V |
| H | A or S |
| L | R, E or S |
| K | V |
| M | L or W |
| F | T |
| P | C or V |
| T | N, G, K, M, F, S or T |
| W | C, E, I, K, S or Y |
| Y | R, H, W or V |
| V | D or S |

Alternatively, in some embodiments, the amino acid residues of the polypeptide corresponding to the amino acid at positions 2 and 18 of endostatin, respectively, are selected from the following combinations:

| Amino acid residue at position 2 | Amino acid residue at position 18 |
|---|---|
| A | Q or H |
| R | L or Y |
| N | T |
| D | V |
| C | P or W |
| E | D, L or W |
| G | T |
| H | Q or Y |
| I | R or W |
| L | M |
| K | N, T or W |
| M | A, D or T |
| F | T |
| S | E, H, L, T, W or V |
| T | D, F or T |
| W | M or Y |
| Y | D or W |
| V | E, K, P or Y |

It should be understood that "fragment" refers to a portion of continuous sequence from a full-length sequence. For example, the polypeptide of the present disclosure preferably is a sequence consisted of amino acid residue 1 to amino acid residue at position 20, 21, 22, 23, 24, 25, 26, 27, 28, 29, 30, 31, 32, 33, 34, 35, 36, 37, 38, 39, 40, 41, 42, 43, 44 or 45 of the N terminus of endostatin and having the indicated amino acid residues at positions 2 and 18 as disclosed herein. In other words, the polypeptide of the present disclosure contains 20-45 amino acid residues, counted from the first amino acid residue of the N terminus of endostatin. More preferably, the length of the polypeptide of the present disclosure is 25-40 amino acid residues, counted from the first amino acid residue of the N terminus of endostatin.

In some embodiments, in addition to the amino acid residues at positions 2 and 18, the fragment may optionally contain the following amino acid residue(s) at any one, two, three or all four of positions 17, 20, 21 and 22:

Amino acid residue at position 17: S, A, L, I, V or T;
Amino acid residue at position 20: S or T;
Amino acid residue at position 21: G, A, L, I or V;
Amino acid residue at position 22: G, A, L, I or V.

Therefore, in some embodiments, the polypeptide of the present disclosure, as a fragment of 45 or less amino acid residues of the N terminus of endostatin, contains at least amino acid residues 1-22, preferably amino acid residues 1-25, of SEQ ID NO: 38, and amino acid residues at positions 2 and 18 are those as defined herein, and amino acid residues at any one, two, three or all four of positions 17 and 20-22 are those as defined above. More specifically, such polypeptides consist of 25-40 amino acid residues.

In some embodiments, the polypeptide of the present disclosure, as a fragment of 45 or less amino acid residues of the N terminus of endostatin, contains at least amino acid residues 1-22, preferably amino acid residues 1-25, of SEQ ID NO: 38, and the amino acid residue at position 2 is T, the amino acid residue at position 18 is N, G, K, M, F, S or T, preferably N or S, and optionally, the amino acid residues at positions 17 and 20-22 are those as defined above. More specifically, such polypeptides consist of 25-40 amino acid residues.

In some embodiments, the polypeptide of the present disclosure, as a fragment of 45 or less amino acid residues of the N terminus of endostatin, contains at least amino acid residues 1-22, preferably amino acid residues 1-25, of SEQ ID NO: 38, and the amino acid residue at position 18 is N, the amino acid residue at position 2 is T, and optionally, the amino acid residues at positions 17 and 20-22 are those as defined above. More specifically, such polypeptides consist of 25-40 amino acid residues.

In some embodiments, the polypeptide of the present disclosure, as a fragment of 45 or less amino acid residues of the N terminus of endostatin, contains at least amino acid residues 1-22, preferably amino acid residues 1-25, of SEQ ID NO: 38, and the amino acid residue at position 18 is S, the amino acid residue at position 2 is E, H, L, T, W or V, and optionally, the amino acid residues at positions 17 and 20-22 are those as defined above. More specifically, such polypeptides consist of 25-40 amino acid residues.

The amino acid sequences of the preferred polypeptide of the present disclosure are set forth in SEQ ID NO: 4, 5, 6, 7, 27-30, 39 and 41. The polypeptides of the present disclosure also include the amino acid sequences consisting of amino acid residue 1 to residue 39, 38, 37, 36, 34, 33, 32, 31, 29, 28, 27 or 26 of SEQ ID NO: 4, and amino acid sequences consisting of amino acid residue 1 to amino acid residue 39, 38, 37, 36, 35, 34, 33, 32, 31, 29, 28, 27, 26 or 25 of SEQ ID NO: 39.

The first amino acid residue at the N terminus of the present polypeptide is histidine, which can be modified by formylation, acetylation, propionylation or butyrylation, and the first amino acid in the C terminus may be modified by PEG, cholesterol or amidation.

Preferably, the first amino acid residue at the N terminus of the present polypeptide, histidine, is modified by acetylation, and the first amino acid in the C terminus is modified by amidation.

It should be understood that suitable restriction sites need to be designed often during gene cloning, with which one or more irrelevant residues will necessarily be introduced to the end of the expressed amino acid sequence. However, such introduction will not affect the activity of the target sequence. Additionally, to construct a fusion protein, to facilitate expression of a recombination protein, to obtain a recombinant protein which voluntarily secretes outside the host cell or to facilitate the purification of a recombinant protein, generally some amino acids, such as but is not limited to a suitable linker, a signal peptide, a leader peptide, a terminal extension, etc., need to be added to the N terminus, C terminus or the other suitable portion of the recombination protein. The amino terminus or the carboxyl terminus of the present amino acid sequences could further comprise one or more polypeptide fragments, as a protein tag. Any suitable tag can be used in the present disclosure. Such tag may be, such as FLAG, HA, HA1, c-Myc, Poly-His, Poly-Arg, Strep-TagII, AU1, EE, T7, 4A6, ε, B, gE and Ty1. Such tags can be used in protein purification. Examples of the used tags include Poly-Arg, such as RRRRR (SEQ ID NO: 42); Poly-His 2-10 (generally 6), such as HHHHHH (SEQ ID NO: 43); FLAG, i.e., DYKDDDDK (SEQ ID NO: 44); Strep-TagII, i.e., WSHPQFEK (SEQ ID NO: 45); and C-myc, i.e., WQKLISEEDL (SEQ ID NO: 46).

Therefore, the present disclosure also comprises the polypeptides comprising the tag sequence or the polypeptides consisting of the tag sequence and the above-mentioned fragment.

The amino acid sequence of the present invention may be a chemically synthesized product or a recombinant polypeptide produced by recombinant technique from prokaryotic host cell or eukaryotic host cell, such as bacterium, yeast, filamentous fungi or cells from higher plant, insect or mammal. According to the cells used in the recombinant protocol, the polypeptide of the present disclosure may be glycosylated or non-glycosylated.

For example, the amino acid sequence of the present disclosure may be synthesized by the peptide chemical synthesis method known in the art. The peptide chemical synthesis comprises solid phase synthesis and liquid phase synthesis, with the solid phase synthesis being commonly used. The solid phase synthesis includes but is not limited to two commonly used methods, Fmoc and tBoc. Generally, resin is used as an insoluble solid support and amino acid is conjugated to the peptide chain from the C terminus (carboxyl terminus) to the N terminus (amino terminus) one by one. Each cycle for amino acid connection consists of the following three steps: 1) de-protection, in which the protective group of the amino on the protected amino acid must be removed by a de-protective solvent; 2) activation, in which the carboxyl group of the amino acid to be conjugated is activated by an activator; and 3) conjugation, in which the activated carboxyl group reacts with the exposed amino group of the previous amino acid to form a peptide bond. The cycle is repeated until the peptide extends to the desired length. Cleaving solution is used to cleave the linkage between the peptide chain and the solid support, thus obtaining the desired amino acid sequence. The chemical synthesis can be carried out in a program-controlled, automatic peptide synthesizer, which includes but is not limited to Tribute dual channel peptide synthesizer from Protein Technologies, UV Online Monitor system from C S Bio, and Focus XC three channel synthesizer from Aapptec, etc.

Also included are the polynucleotides encoding the polypeptides of the present disclosure. For example, SEQ ID NO: 30 shows a coding sequence for SEQ ID NO: 1; SEQ ID NO: 31 shows a coding sequence for SEQ ID NO: 3; SEQ ID NO: 32 shows a coding sequence for SEQ ID NO: 4; SEQ ID NO: 33 shows a coding sequence for SEQ ID NO: 5; SEQ ID NO: 34 shows a coding sequence for SEQ ID NO: 6; SEQ ID NO: 35 shows a coding sequence for SEQ ID NO: 7; SEQ ID NO: 36 shows a coding sequence for SEQ ID NO: 8; SEQ ID NO: 37 shows a coding sequence for SEQ ID NO: 9; and SEQ ID NO: 40 shows a coding sequence for SEQ ID NO: 39.

The polynucleotide of the present disclosure may be in a form of DNA or RNA. DNA includes cDNA, genomic DNA or synthesized DNA. DNA may be a single-stranded or a double-stranded DNA. DNA may be a coding strand or a non-coding strand. Coding sequence encoding a mature polypeptide may be identical to the above-mentioned DNA sequence or may be a degenerated variant. "Degenerated variant", as used herein, refers to a nucleic acid encoding the amino acid sequence of the present disclosure but has a different nucleotide sequence from those such as SEQ ID NO: 31, etc.

The term "polynucleotide encoding polypeptide" may include the polynucleotide encoding the polypeptide, or polynucleotide further containing additional coding and/or non-coding sequence.

The polypeptide and polynucleotide of the present disclosure may be provided in an isolated form. Preferably they are purified to homogeneous substance.

Generally, the polynucleotide of the present disclosure is obtained by PCR amplification, recombination or artificial synthesis. For the PCR amplification, primers could be designed according to the nucleotide, especially the sequence of the open reading frame, disclosed in the present disclosure. The cDNA library commercially available or the cDNA library prepared by the skilled artisan according to the conventional method could be used as template to amplify the related sequence. Generally, two or more PCR amplifications are carried out for the long sequence and then the fragments obtained from each amplification are ligated together in a proper order.

Once a sequence of interest is obtained, it could be produced in large quantity through a recombinant method. Generally, the sequence is cloned into a vector, which is then transfected into cells. And the related sequence is isolated from the proliferative host cell via conventional method.

Alternatively, the sequence may be synthesized by an artificial synthesis, especially when the fragment is short. Generally, several small fragments are firstly synthesized and then they are ligated together to form a long fragment.

Currently, the DNA sequence encoding the amino acid sequence of the present disclosure may be obtained by chemical synthesis. Then the DNA sequence may be introduced to various existing DNA molecules, such as vector, and cells known in the art.

The present disclosure also directs to the vector comprising the polynucleotide of the present disclosure, the host cell produced from the vector of the present disclosure via genetic engineering, and the method for producing the polypeptide of the present disclosure via a recombinant technique. Preferably, the vector of the present disclosure is an expression vector.

The polypeptide of the present disclosure may be expressed or produced from the polynucleotide of the present disclosure via a conventional recombinant DNA technique, which generally comprises the following steps:

(1) transforming or transfecting suitable host cells with the polynucleotide or its degenerated variant, or the recombinant expression vector containing said polynucleotide of the present disclosure;

(2) culturing the host cell in a suitable culture medium; and (3) isolating and purifying the protein from the culture medium or the cells.

The polynucleotide sequence of the present disclosure may be inserted into a recombinant expression vector. The term "recombinant expression vector" refers to the well-known bacterial plasmid, bacteriophage, yeast plasmid, viruses of plant cell or mammal cell, such as adenovirus and retrovirus, or other vectors. Any plasmid and vector can be used as long as it can replicate and is stable in the host. One important feature for the expression vector is that it generally contains a replication origin, a promoter, a marker gene and an element for controlling translation. An expression vector may further comprise ribosome binding site for initiating translation and transcription terminator.

Methods known in the art may be used to construct an expression vector comprising the nucleic acid sequence of the present disclosure and suitable transcription/translation control signal. These methods include in vitro recombinant DNA technique, DNA synthesis, and in vivo recombinant technique, etc. The nucleic acid sequence may be effectively linked to a suitable promoter in the expression vector to direct synthesis of mRNA. Examples of such promoter include *E. coli* lac or trp promoter, λ phage PL promoter; eukaryotic promoter, such as CMV immediate early promoter, HSV thymidine kinase promoter, early or late SV40 promoter, retrovirus LTR and other promoters known capable of controlling gene expression in prokaryotic cell, eukaryotic cell or virus.

Additionally, the expression vector preferably comprises one or more selection marker genes to provide the phenotypic character for selecting the transformed host cell, which may include dihydrofolate reductase, neomycin resistance and green fluorescent protein for culture of eukaryotic cell, or tetracycline or ampicillin resistance for *E. coli*.

Vector comprising the above suitable DNA sequence and suitable promoter or control sequence may be used to transform a suitable host cell to make it to express a protein.

Host cell may be a prokaryotic cell, such as bacterial cell; or a lower eukaryotic cell, such as yeast cell, filamentous fungal cell; or advanced eukaryotic cell, such as mammal cell. Representative examples include *E. coli, Streptomyces, Salmonella typhimurium*; fungi, such as yeast, filamentous fungi; plant cell; insect cell, such as drosophila S2 or Sf9 cell; animal cell, such as CHO, COS, 293 or Bowes melanoma cell, etc.

When the polynucleotide of the present invention is expressed in an advanced eukaryotic cell, an enhancer sequence may be inserted into the vector to enhance the transcription. The enhancer may be a cis-acting element of DNA, generally comprising about 10 to 300 bp and being used as a promoter to enhance the transcription of the gene.

The skilled artisan knows how to select suitable vector, promoter, enhancer and host cell.

Transformation of host cell by a recombinant DNA could be carried out by a conventional technique known to the skilled artisan. When the host is a prokaryotic organism, such as E. coli, competent cells which can adsorb DNA are harvested after their exponential growth phase and treated by a $CaCl_2$ method. The steps used are well known in the art. Another method is to use $MgCl_2$. If desired, transformation can also be carried out by electroporation. When the host is a eukaryotic organism, the following DNA transfection methods could be used: calcium phosphate co-precipitation or conventional mechanical methods such as microinjection, electroporation and liposome packaging, etc.

The resultant transformant could be cultured by a conventional method to express the polypeptide encoded by the gene of the present disclosure. According to the host cell used, the culture medium may be various conventional culture mediums. Cells were culture under conditions suitable for growth of the host cell. When the host cells grow to a suitable cell density, the selected promoter is induced by a suitable method, such as change of temperature or chemical induction, and the cells are further cultured for a period of time.

The recombinant polypeptide of the above-mentioned method could be expressed within the cell or on the cell membrane, or secreted outside the cell. If necessary, the recombinant protein could be isolated and purified by utilizing its physical, chemical or other properties through various isolation methods. All these methods are well known by the skilled artisan. Examples of these methods include but are not limited to a conventional renaturation treatment, treatment by protein precipitant (salt out method), centrifugation, osmosis method for breaking cell, ultrasonic processing, ultracentrifugation, sieve chromatography (gel filtration), adsorption chromatography, ion exchange chromatography, high performance liquid chromatography (HPLC) or other various liquid chromatography techniques, and combination thereof. Methods for preparing a polypeptide via a recombinant technique are known in the art.

The present disclosure also provides a pharmaceutical composition, comprising the polypeptide of the present disclosure and a pharmaceutically acceptable carrier.

The pharmaceutical composition comprises the polypeptide of the present disclosure in a therapeutically or prophylactically effective amount. The term "effective amount" refers to the quantity of a component which is sufficient to produce a desired response. The specific effective amount will vary with such factors as the particular disease to the treated, the physical condition of the subject, such as weight, age and gender, the duration of the treatment, the nature of concurrent therapy (if any) and the specific formulations employed. The "effective amount" is also one in which any toxic or detrimental effects of the compound or composition are outweighed by the therapeutically beneficial effects.

The pharmaceutically acceptable carrier is generally safe, non-toxic, and in a broad sense, may also include any known substance in the pharmaceutical industry useful for preparing pharmaceutical compositions, such as fillers, diluents, aggluatinants, binders, lubricating agents, glidants, stabilizers, colorants, wetting agents, disintegrants, and etc. The choice of an excipient used for delivering a synthetic peptide is basically determined by the way the pharmaceutical composition is to be administered, and this is well known by the skilled artisan.

The amount of the polypeptide in the pharmaceutical composition of the present disclosure may be about 0.01-1000 μM.

The pharmaceutical composition is prepared in accordance with acceptable pharmaceutical procedures, such as described in Remington's Pharmaceutical Science, $17^{th}$ edition, ed. Alfonoso R. Gennaro, Mack Publishing Company, Easton, Pa. (1985).

The pharmaceutical composition of the present disclosure may be formulated into various suitable dosage forms, including but is not limited to tablet, capsule and injection, etc.

The pharmaceutical composition of the present disclosure may contain the other known chemotherapeutic agent, especially those used for treating or preventing tumor, including but is not limited to cisplatin, carboplatin or oxaliplatin.

The polypeptide and pharmaceutical composition of the present disclosure may be used to treat or prevent various diseases that were known to be treated or prevented by endostatin, to alleviate or relieve various symptoms that are known to be alleviated or relieved by endostatin.

For example, the polypeptide and pharmaceutical composition of the present disclosure may be administered to the subject in need thereof for treating or preventing tumor. The subject may be a mammal, especially human being.

Tumor includes angioneoplasm and solid tumors. The solid tumors include but are not limited to rhabdomyosarcoma, retinoblastoma, Ewing sarcoma, neuroblastoma, osteosarcoma, lung carcinoma, lung squamous cell carcinoma, liver cancer, color cancer, and pancreatic cancer.

The present disclosure also provides a method for treating cancer, comprising administering a subject in need thereof the polypeptide or pharmaceutical composition of the present disclosure.

The present disclosure also provides a method for enhancing the efficacy of a chemotherapeutic agent, comprising administering a subject in need thereof the polypeptide or pharmaceutical composition of the present disclosure before, at the same time of, or after administering the chemotherapeutic agent Also provided is use of the polypeptide or pharmaceutical composition of the present disclosure in the manufacture of a medicament for treating or preventing tumor.

Also provided is use of the polypeptide or pharmaceutical composition of the present disclosure in the manufacture of a medicament for enhancing the efficacy of a chemotherapeutic agent.

Also provided is the polypeptide described in various aspects or various embodiments of the present disclosure for use as a medicament. Also provided is the polypeptide described in various aspects or various embodiments of the present disclosure for use in treating or preventing tumor as described in the present disclosure or in enhancing the efficacy of a chemotherapeutic agent.

EXAMPLE

The present invention will be further illustrated in combination with the following specific examples. The practice of the present invention will employ, unless otherwise indicated, conventional methods of chemistry, biochemistry, recombinant DNA techniques and immunology, within the skill of the art. Such techniques are explained fully in the literature. See, e.g., Peptide: Chemistry and Biology, N. Sewald and H. D. Jakubke eds., translated by L I U Keliang and H E Junlin et al., Science Press; Fundamental Virology, $2^{nd}$ Edition, vol. I & II (B. N. Fields and D. M. Knipe, eds.); Handbook of Experimental Immunology, Vols. I-IV (D. M. Weir and C. C. Blackwell eds., Blackwell Scientific Publications); T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.). Additionally, it should be understood that the term "comprise", "contain" or similar wording also includes "consist of". The sequence numbers "SEQ ID NO: 1-29, 38, 39 and 41" merely indicate an amino acid sequence without the N terminal modification and the C terminal modification.

Example 1: Preparation and Modification of Polypeptides

Polypeptides having the amino acid sequences shown in the Table below were synthesized according to the standard Fmoc protocol for polypeptide synthesis by extending individual residues from the carboxyl terminus to the amino terminus, starting from a 0.25 mM resin. The N terminus was modified finally. After completion of peptide synthesis, the polypeptides were cleaved from the resin by a cleavage solution and the resin was removed by filtering with G6 sand-core funnel. The filtrate was dried under vacuum and the C terminus of the polypeptides could further be amidated. The polypeptide product was dissolved in deionized water, and purified in ÄKTA explorer 100 type medium pressure liquid chromatograph equipped with C18 column. The main peaks were recovered stepwise. The samples collected from the target peak were analyzed by Agilent 1100 type reversed phase high pressure liquid chromatography equipped with Phenomenex C18 column for their purities and identified by LCQ Advantage type mass spectrograph for their molecular weights. The collecting solutions purified by medium pressure liquid chromatography was freeze dried and dissolved in PBS to form a polypeptide stock, which was then filtered through a 0.20 μM membrane and stored at −80° C. Purities identified by HPLC and molecular weights identified by MASS spectrometry were shown in FIG. 1.

20 cm umbilical cord adjacent to fetus was taken, cleaned by washing, ligated at both ends, placed into 150 ml preservation solutions for umbilical cord, and stored in a 4° C. refrigerator for digestion for 6 hours. The umbilical cord was inspected to remove the damaged portion. The umbilical vein was thoroughly cleaned by washing and then 10 ml collagenase solution was injected. Then the umbilical vein was transferred to a 37° C. incubator for digestion for 15 minutes. The umbilical cord was removed and the digested solution was recovered. The digested solution was washed by PBS and centrifuged. After centrifugation, the cells were culture by re-suspension. Culture medium was replaced after 24 hours and the cells that did not adhere to the wall were removed.

Example 3: Inhibition of Polypeptides on Human Umbilical Vein Endothelial Cell (HUVEC) and Tumor Cell Inhibition of cell growth was detected by a MTT method, which is based on the principle that succinate dehydrogenase in the mitochondria of the live cells could reduce the exogenous MTT (3-(4,5-dimethyl-2-thiazolyl)-2,5-diphenyl-tetrazolium bromide) to a water-soluble Formazan which is a blue-violet crystal, and precipitates in the cells, while the death cells could not reduce MTT. DMSO could dissolve Formazan in the cells. Absorbance value of the solution was determined at 490/570 nm by microplate reader, which could indirectly indicate the amount of the live cells. The amount of the crystal from MTT is proportional to the amount of the cells within a certain range of cell number. The supernate from the HUVEC or tumor cells in exponential phase was removed and the cells were washed by PBS once. 1 ml 0.25% trypsin (4° C.) was added for digestion at 37° C. for 2 min. Then the supernate was added for neutralization and the cells were dispersed to form a suspension and the suspension was centrifuged at 1000 rpm for 3 min. The supernate was removed and 5 ml culture mediums were

| No. of Polypeptide | No. of Sequence | Sequence (from N terminus to C terminus) |
|---|---|---|
| P1 | SEQ ID NO: 2 | HSHRDFQPVLHLVALNSPLSGGMRGIRGAD |
| P2 | SEQ ID NO: 47 | Ac-HSHRDFQPVLHLVALNSPLSGGMRGIRGAD-NH$_2$ |
| P2T2S18 | SEQ ID NO: 6 | Ac-H<u>T</u>HRDFQPVLHLVALNS<u>S</u>LSGGMRGIRGAD-NH$_2$ |
| P2T2N18 | SEQ ID NO: 9 | Ac-H<u>T</u>HRDFQPVLHLVALNS<u>N</u>LSGGMRGIRGAD-NH$_2$ |

Example 2: Isolation and Culture of Human Umbilical Vein Endothelial Cell (HUVEC)

Preparation of a preservation solution for umbilical cord: 150 ml PBS+3× (working concentration) double antibody (Penicillin/Streptomycin).

Preparation of complete medium: 80 ml M199+20 ml FBS+1 ml ECGS+1 ml 100× double antibody+1 ml heparin solution (0.5% W/V)+1 ml 200 mM glutamine.

Preparation of separation apparatus: one surgical kidney basin, 4-5 vessel forceps, 2 surgical scissors, glass culture dish having a diameter of about 10 cm;

Formulation of type I collagenase: formulated to 1% (v/v).

added for resuspension. Cells were inoculated in a 48-well plate by 500 ul/well at the concentration of 3×10$^4$/ml and then incubated under 5% CO$_2$, 37° C. for 24 hours. The supernate was removed and a culture medium containing polypeptide (Zn$^{2+}$ in the culture medium was present at the concentration of 17.39 μmol/L) was added for further incubation for 48 hours. Supernate in each well was carefully removed. The well was gently washed by PBS once in an amount of 450 μl/well. 450 μl MTT culture mediums were added into each well for further cultivation for 4 hours. The supernate was carefully discarded. DMSO was added in an amount of 450 μl/well and then the plate was placed in a shaking bed for oscillation for 10 min in dark. 150 μl supernates were transferred to a 96-well ELISA plate and absorbance value of each well was detected at 490 nm and 570 nm by the microplate reader.

Example 4: Effect of Modification at the N Terminus and the C Terminus of the Polypeptide on its Activity Polypeptides, the amino acid sequence of which is set forth in the following Table (SEQ ID NO: 2), were synthesized by the methods disclosed in Example 1, which may have or have no modification at N and/or C terminus. Ac indicates acetylation modification, $NH_2$ indicates amidation modification. Purities of these polypeptides were identified by HPLC and their molecular weights were identified by MASS spectrometry.

| No. of Polypeptide | Sequence (from N terminus to C terminus) |
|---|---|
| P1 (SEQ ID NO: 2) | HSHRDFQPVLHLVALNSPLSGGMRGIRGAD |
| P2 (SEQ ID NO: 47) | Ac-HSHRDFQPVLHLVALNSPLSGGMRGIRGAD-NH$_2$ |
| P3 (SEQ ID NO: 6) | Ac-HSHRDFQPVLHLVALNSPLSGGMRGIRGAD |
| P4 (SEQ ID NO: 9) | HSHRDFQPVLHLVALNSPLSGGMRGIRGAD-NH$_2$ |

Recombinant human endostatins (endostatin, SEQ ID NO: 1) could be commercially available, for example, from Genetex (Article No. GTX 65524), BioVision (Article No. 4799-1000), Shanghai Biosun Sci&Tech Co., Ltd. (Article No. E2296-05), and Wuhan Boster Bio-engineering Co., Ltd. (Article No. BP4153). The marketed recombinant human endostatin drug, endostar (SEQ ID NO: 10), was purchased from a medical institution.

Figure 2:
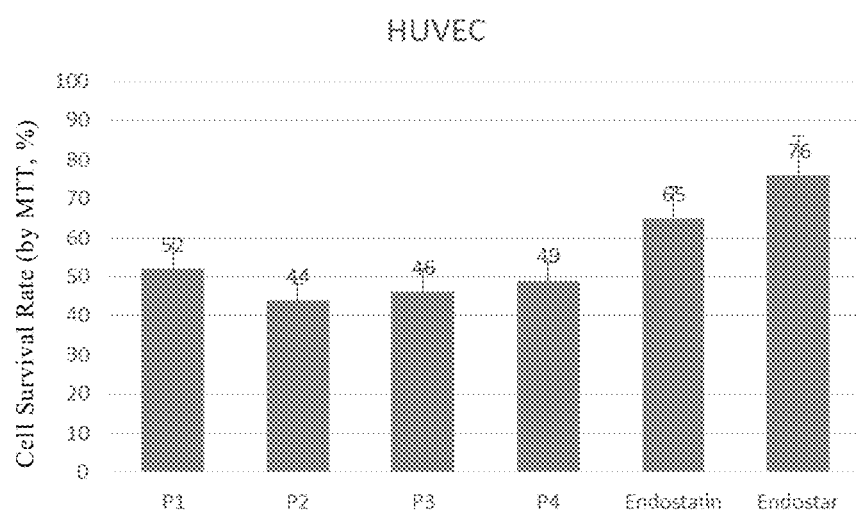
FIG. 2 illustrates the biological activities of P1, P2, P3, P4, endostatin and endostar in inhibiting HUVEC.
Figure 3A:
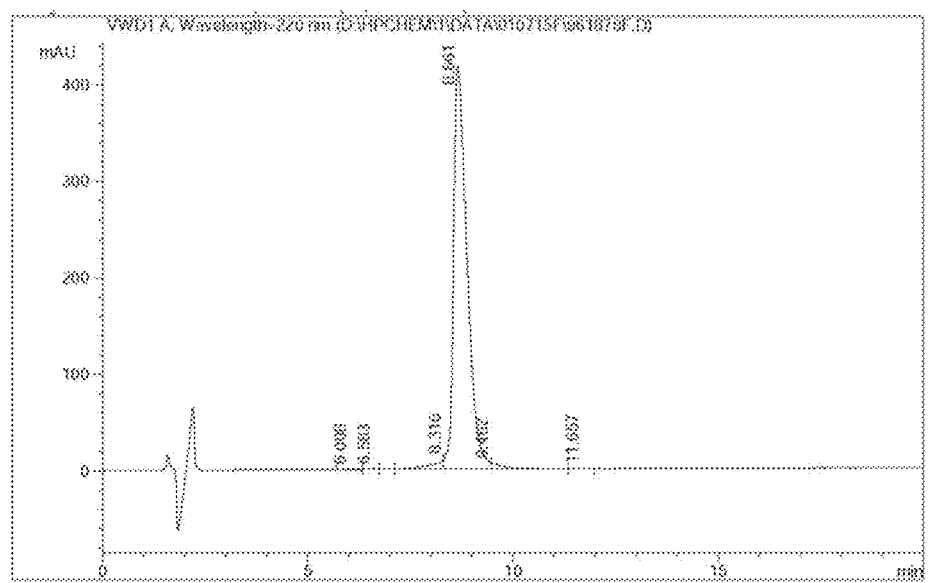
FIGS. 3a and 3b illustrate the HPLC and MASS maps of polypeptide P2T2S18Δ1, respectively.
Figure 3B:
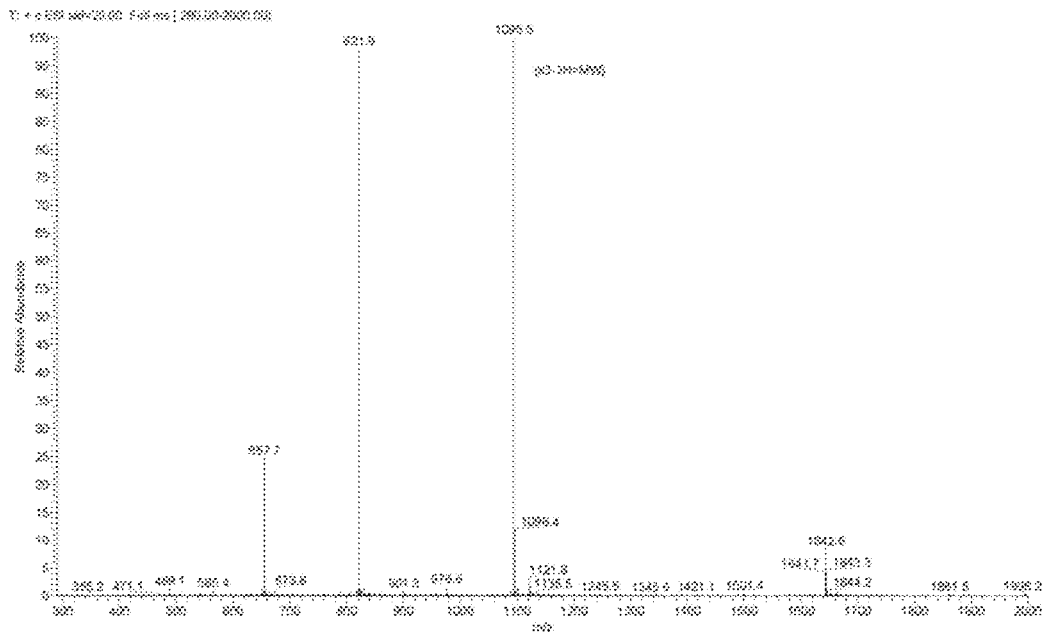
Figure 3C:
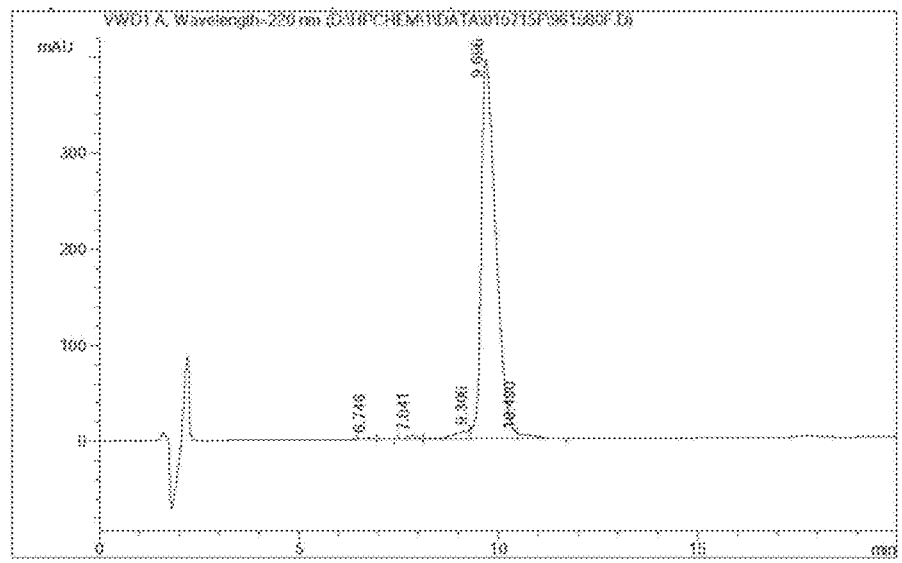
FIGS. 3c and 3d illustrate the HPLC and MASS maps of polypeptide P2T2S18Δ2, respectively.
Figure 3D:
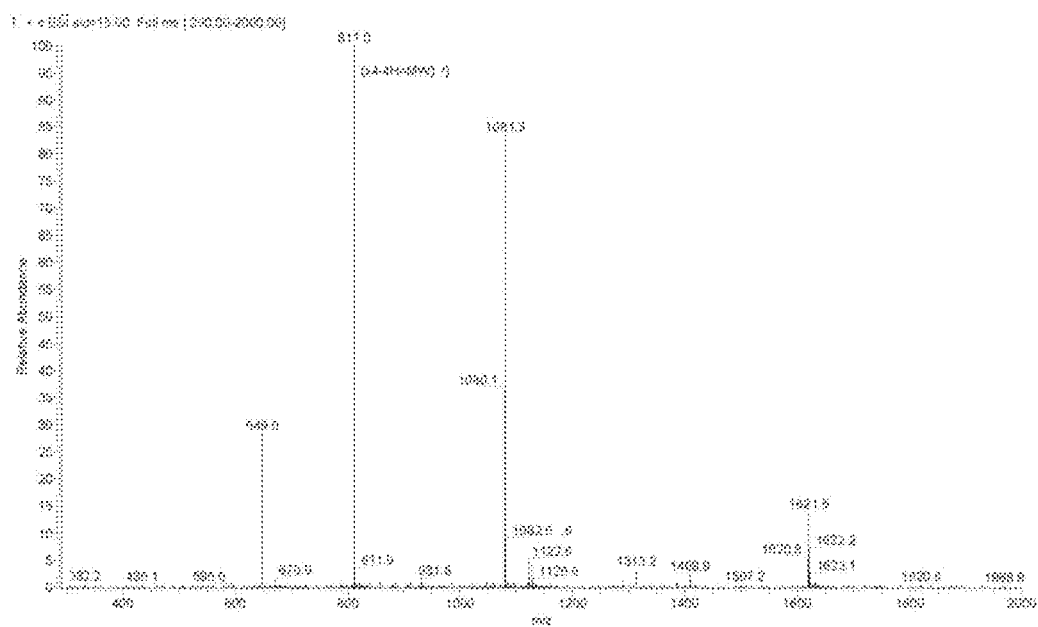
Figure 3E:
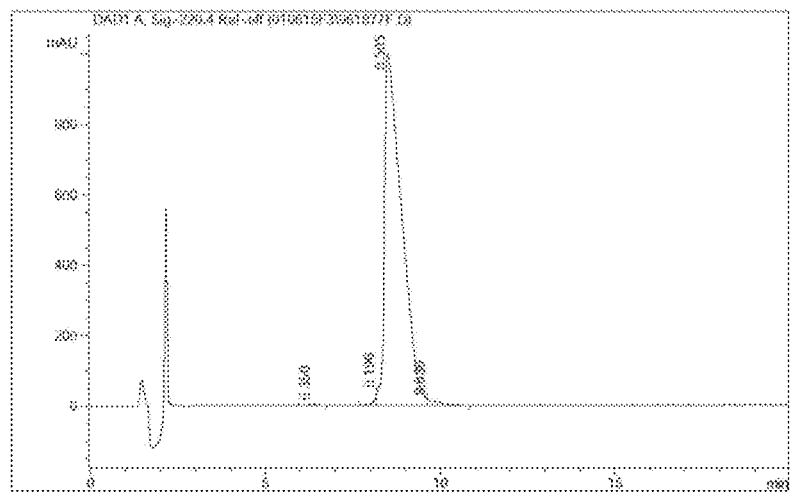
FIGS. 3e and 3f illustrate the HPLC and MASS maps of polypeptide P2T2S18Δ3, respectively.
Figure 3F:
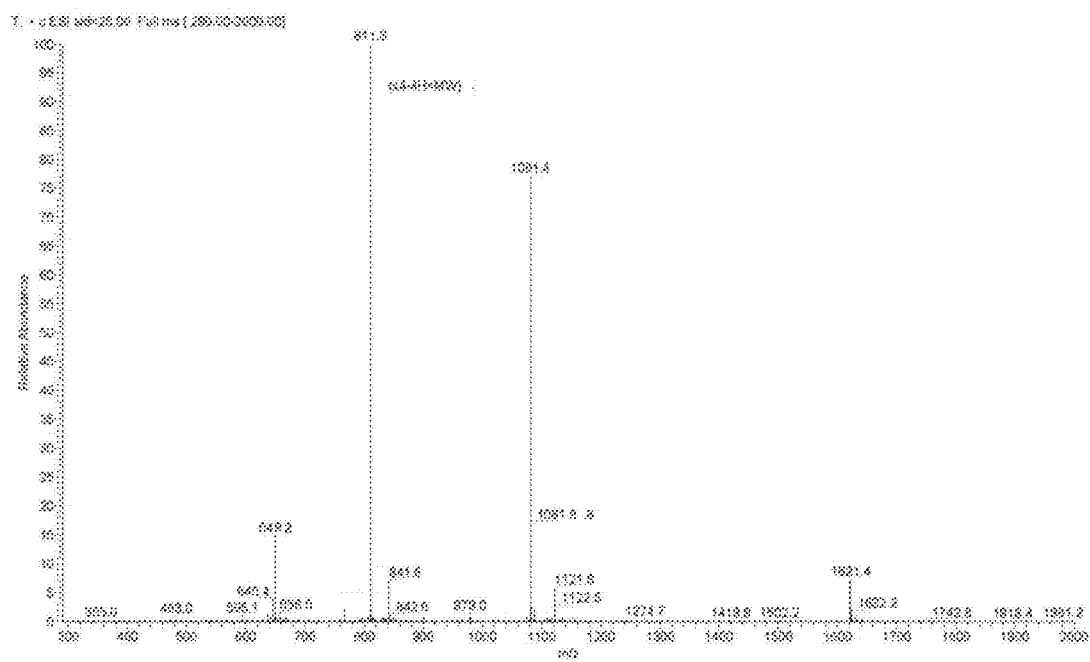

Biological activities of P1, P2, P3, P4, endostatin and endostar in inhibiting HUVEC were detected according to the method described in Example 3 under the condition that the polypeptides were used in 1 mg/ml and the recombinant human endostatin was used in 5 mg/ml (the polypeptides and endostatins had basically equal molar concentrations). Results were shown in FIG. 2.

Example 5: Study on Structure-Efficacy Relationship of Polypeptides

Figure 4:
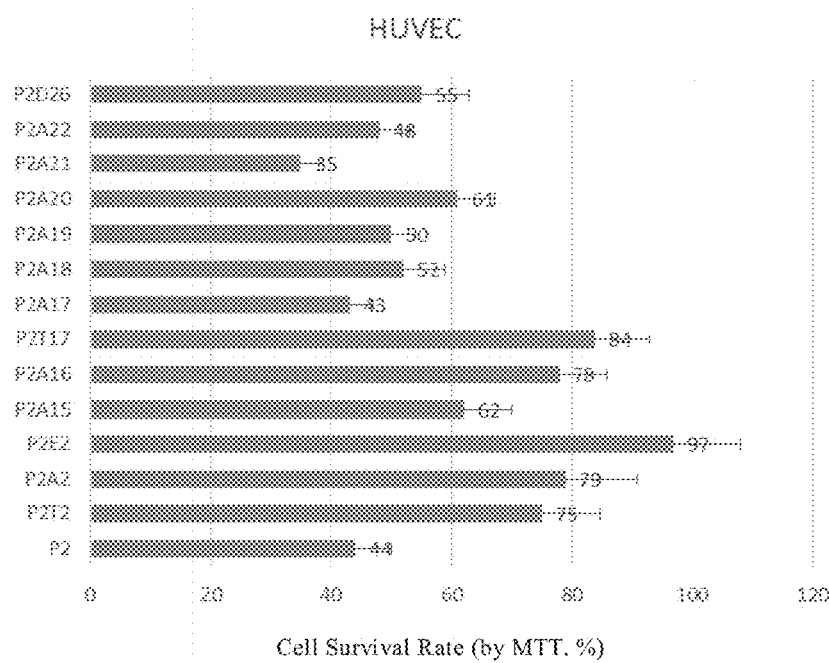
FIG. 4 illustrates the biological activities of some polypeptides in inhibiting HUVEC.

Polypeptides shown in the Table below were synthesized according to the method described in Example 1. Their purities were identified by HPLC and their molecular weights were identified by MASS spectrometry. Biological activities of these polypeptides in inhibiting HUVEC at a concentration of 1 mg/ml were tested according to the method described in Example 3. Results are shown in FIG. 4.

| No. of Polypeptide | No. of Sequence | Sequence (from N terminus to C terminus) |
|---|---|---|
| P2 | SEQ ID NO: 47 | Ac-HSHRDFQPVLHLVALNSPLSGGMRGIRGAD-NH$_2$ |
| P2T2 | SEQ ID NO: 11 | Ac-HTHRDFQPVLHLVALNSPLSGGMRGIRGAD-NH$_2$ |
| P2A2 | SEQ ID NO: 12 | Ac-HAHRDFQPVLHLVALNSPLSGGMRGIRGAD-NH$_2$ |
| P2E2 | SEQ ID NO: 13 | Ac-HEHRDFQPVLHLVALNSPLSGGMRGIRGAD-NH$_2$ |
| P2A15 | SEQ ID NO: 14 | Ac-HSHRDFQPVLHLVAANSPLSGGMRGIRGAD-NH$_2$ |
| P2A16 | SEQ ID NO: 15 | Ac-HSHRDFQPVLHLVALASPLSGGMRGIRGAD-NH$_2$ |
| P2T17 | SEQ ID NO: 16 | Ac-HSHRDFQPVLHLVALNTPLSGGMRGIRGAD-NH$_2$ |
| P2A17 | SEQ ID NO: 17 | Ac-HSHRDFQPVLHLVALNAPLSGGMRGIRGAD-NH$_2$ |
| P2A18 | SEQ ID NO: 18 | Ac-HSHRDFQPVLHLVALNSALGGMRGIRGAD-NH$_2$ |
| P2A19 | SEQ ID NO: 19 | Ac-HSHRDFQPVLHLVALNSPASGGMRGIRGAD-NH$_2$ |
| P2A20 | SEQ ID NO: 20 | Ac-HSHRDFQPVLHLVALNSPLAGGMRGIRGAD-NH$_2$ |
| P2A21 | SEQ ID NO: 21 | Ac-HSHRDFQPVLHLVALNSPLSAMRGIRGAD-NH$_2$ |
| P2A22 | SEQ ID NO: 22 | Ac-HSHRDFQPVLHLVALNSPLSGAMRGIRGAD-NH$_2$ |
| P2D26 | SEQ ID NO: 23 | Ac-HSHRDFQPVLHLVALNSPLSGGMRGDRGAD-NH$_2$ |

The above polypeptides were subjected to homology modeling via software INSIGHT II based on the structure of endoestatin disclosed in EMBO J. 1998 Mar. 16; 17(6): 1656-1664 (Structural No. in PDB database is 1BNL) to obtain the preferred conformation of the P2 polypeptides. Highest occupied molecular orbital (HOMO) energy and lowest virtual orbital (LUMO) energy of the P2 polypeptides were calculated via complete active space self-consistent field (CASSCF). Based on above work, we adopted 2-D synergistic iterative algorithms in spatial point field (2-D SIASPF) for polypeptide created by ourself to mimic iterative replacement of combinations of every two amino acids for the P2 polypeptide to calculate variance accumulation of electronic density in the Zn ion-binding domain (1H, 3H, 11H) of the polypeptide caused by the replacement. Together with the biological activity of the amino acid combination actually tested, the synergestic relationship of the biological activity between every amino acid at two sites of P2 was scored. Results show that amino acids at positions 2 and 18 of the polypeptide produce highest effect on synergy of biological activity.

Example 6: Effect of Replacement of Amino Acid of the Polypeptide on its Activity Peptide library for P2 polypeptides having different amino acid residues at positions 2 and 18 was constructed. Polypeptides as shown in the following Table were synthesized via Apex396 automated high throughput peptide syntheiszer from AAPPTEC. In the peptide shown in the table below, $X_1$ and $X_3$ are any naturally occurring amino acid, $X_2$ and $X_4$ are S and $X_5$ and $X_6$ are G.

| No. of Polypeptide | Sequence (from N to C terminus) |
|---|---|
| P2X2X18 | Ac-HX$_1$HRDFQPVLHLVALNX$_2$X$_3$LX$_4$X$_5$X$_6$MRGIRGAD-NH$_2$ (SEQ ID NO: 38) |

Biological activities of these polypeptides in inhibiting HUVEC at a concentration of 1 mg/ml were tested according to the method described in Example 3. Results are shown in the Table below.

| Residue at position 2 | Residue at position 18 | | | | | | | | | | | | | | | | | |
|---|---|---|---|---|---|---|---|---|---|---|---|---|---|---|---|---|---|---|
| | A | R | N | D | C | Q | E | G | H | I | L | K | M | F | P | S | T | W | Y | V |
| A | g | i | j | f | g | j | g | j | f | j | i | f | d | j | h | e | f | j | i | f |
| R | j | f | g | f | i | f | h | f | g | d | g | j | g | f | f | e | g | i | g | e |
| N | g | j | g | e | g | e | j | g | f | i | e | d | f | i | h | e | g | f | j | f |
| D | f | i | e | f | j | g | d | f | e | g | j | i | d | e | f | f | d | e | d | i |
| C | g | j | f | i | i | g | j | j | g | e | f | j | g | i | g | j | g | f | i | f |
| Q | d | g | i | f | j | g | g | f | d | h | j | e | f | g | e | i | f | i | g | i |
| E | e | e | h | e | g | f | g | j | f | e | g | i | g | j | j | d | g | f | e | d |
| G | g | f | f | i | f | j | g | f | i | e | f | g | j | e | e | g | e | e | g | f |
| H | d | i | g | e | g | e | g | j | f | g | e | g | f | g | f | d | g | e | f | e |
| I | i | f | i | f | i | j | j | e | j | i | e | f | j | f | d | f | f | j | h | e |
| L | h | d | i | g | j | f | d | g | g | f | e | h | e | g | j | d | g | e | j | e |
| K | f | f | f | e | e | g | i | e | f | j | g | e | j | f | e | f | j | j | f | d |
| M | j | g | e | j | g | e | f | i | j | f | d | f | g | e | j | f | i | d | i | e |
| F | g | e | e | h | f | e | j | f | j | e | g | j | f | j | g | j | d | e | j | g |
| P | e | i | f | i | d | g | e | e | i | e | i | j | g | e | h | e | f | g | f | d |
| S | f | f | e | f | g | j | e | f | g | i | j | f | e | j | e | j | i | g | j | i |
| T | f | j | a | j | e | j | j | d | f | i | f | d | d | d | h | a | d | i | f | i |
| W | j | e | g | f | d | i | d | e | g | d | f | d | g | e | g | d | j | g | d | e |
| Y | i | d | i | e | i | f | j | g | d | h | f | e | f | j | e | e | i | d | f | d |
| V | j | f | h | d | g | j | g | e | g | j | e | e | g | e | j | d | j | e | f | e |

In the Table, small letters a, b, c, d, e, f, g, h, i and j indicate, respectively: a: the cell activity is 0-10%; b: the cell activity is 11-20%; c: the cell activity is 21-30%; d: the cell activity is 31-40%; e: the cell activity is 41-50%; f: the cell activity is 51-60%; g: the cell activity is 61-70%; h: the cell activity is 71-80%; i: the cell activity is 81-90%; j: the cell activity is 91-100%.

Example 7: Polypeptide Inhibition on In Vitro Growth of Tumor Cells and HUVEC Polypeptides shown in the Table below were synthesized according to the method described in Example 1. Their purities were identified by HPLC and their molecular weights were identified by MASS spectrometry.

| No. of Polypeptide | No. of Sequence | Sequence (from N terminus to C terminus) |
|---|---|---|
| P2 | SEQ ID NO: 47 | Ac-HSHRDFQPVLHLVALNSPLSGGMRGIRGAD-NH₂ |
| P2T2S18 | SEQ ID NO: 6 | Ac-HTHRDFQPVLHLVALNSSLSGGMRGIRGAD-NH₂ |
| P2T2N18 | SEQ ID NO: 9 | Ac-HTHRDFQPVLHLVALNSNLSGGMRGIRGAD-NH₂ |
| P2S18 | SEQ ID NO: 25 | Ac-HSHRDFQPVLHLVALNSSLSGGMRGIRGAD-NH₂ |
| P2N18 | SEQ ID NO: 26 | Ac-HSHRDFQPVLHLVALNSNLSGGMRGIRGAD-NH₂ |
| P2T2 | SEQ ID NO: 11 | Ac-HTHRDFQPVLHLVALNSPLSGGMRGIRGAD-NH₂ |

Figure 5A:
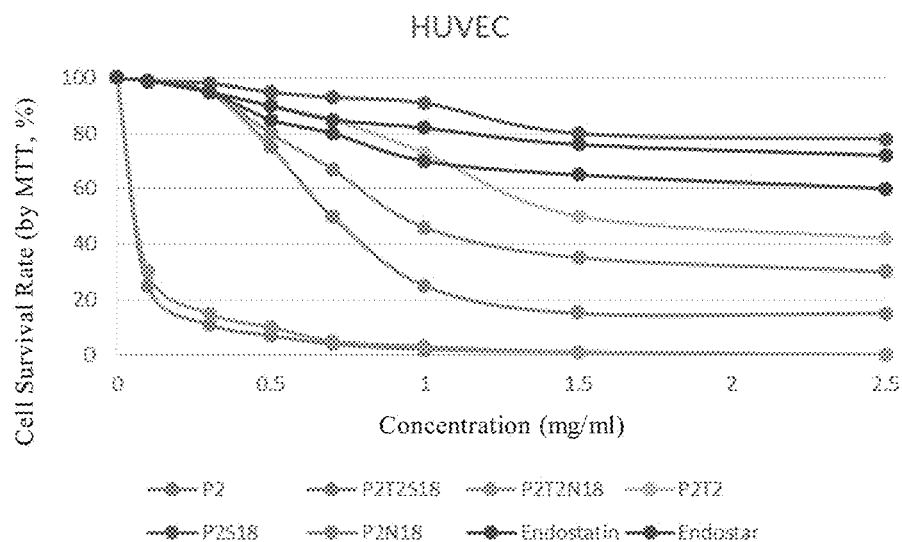
FIGS. 5a and 5b illustrate inhibition of some polypeptides on HUVEC and tumor cell, respectively.
Figure 5B:
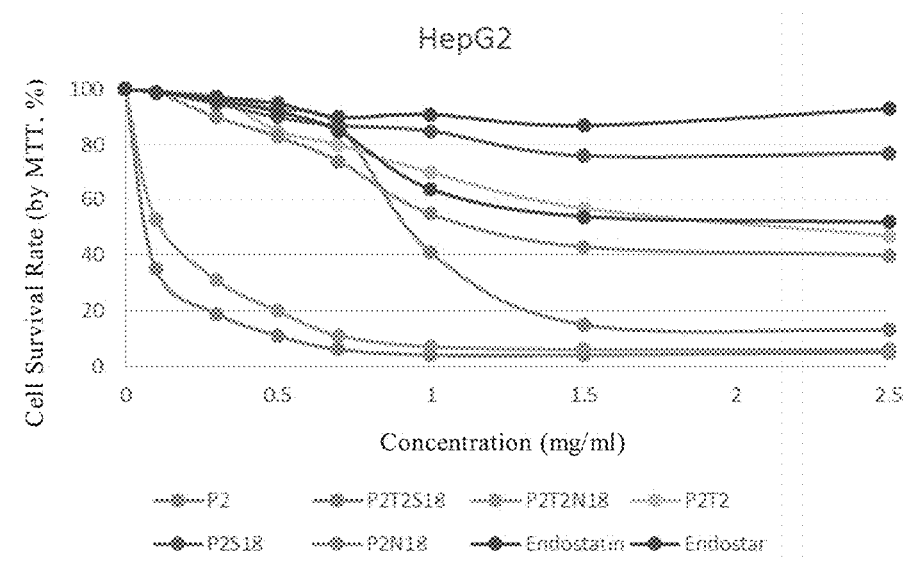

Inhibition on HUVEC and tumor cell HepG2 by recombination endostatin (endostatin) as set forth in SEQ ID NO: 1 and marketed drug endostar as set forth in SEQ ID NO: 10 were tested according to the method described in Example 3. Results were shown in FIGS. 5a and 5b and the following Table. Results show that the biological activities of P2T2S18 and P2T2N18 are obviously higher than that of P2. Their $IC_{50}$ concentrations are reduced by about 10 folds as compared to that of P2. Polypeptide P2T2 having only one mutation at position 2 and polypeptides P2N18 and P2S18 respectively having only one mutation at position 18 exhibit lower biological activity than P2. Therefore, high biological activity of P2T2S18 and P2T2N18 is produced by the unexpected synergistic effect caused by co-mutation on positions 2 and 18. It is difficult to obtain P2T2S18 and P2T2N18 of the present invention with high biological activity using the conventional single point mutation.

| No. of Poly-peptide | No. of Sequence | Cell Survival (%), 1 mg/ml of polypeptide | | $IC_{50}$ (ug/ml) | |
|---|---|---|---|---|---|
| | | HUVEC | HepG2 | HUVEC | HepG2 |
| P2 | SEQ ID NO: 47 | 25 | 41 | 733.4 | 1033.4 |
| P2T2S18 | SEQ ID NO: 6 | 2 | 4 | 66.7 | 76.9 |
| P2T2N18 | SEQ ID NO: 9 | 3 | 7 | 71.4 | 187.9 |
| P2S18 | SEQ ID NO: 25 | 73 | 70 | — | — |
| P2N18 | SEQ ID NO: 26 | 91 | 85 | 1080.8 | 1387.0 |
| P212 | SEQ ID NO: 11 | 46 | 55 | 1506.1 | 2169.6 |
| endostatin | SEQ ID NO: 1 | 70 | 64 | — | 2245.4 |
| endostar | SEQ ID NO: 10 | 82 | 91 | — | — |

Example 8: In Vitro Death of SPC-A-1 Tumor Cell Induced by Polypeptide

Figure 6:
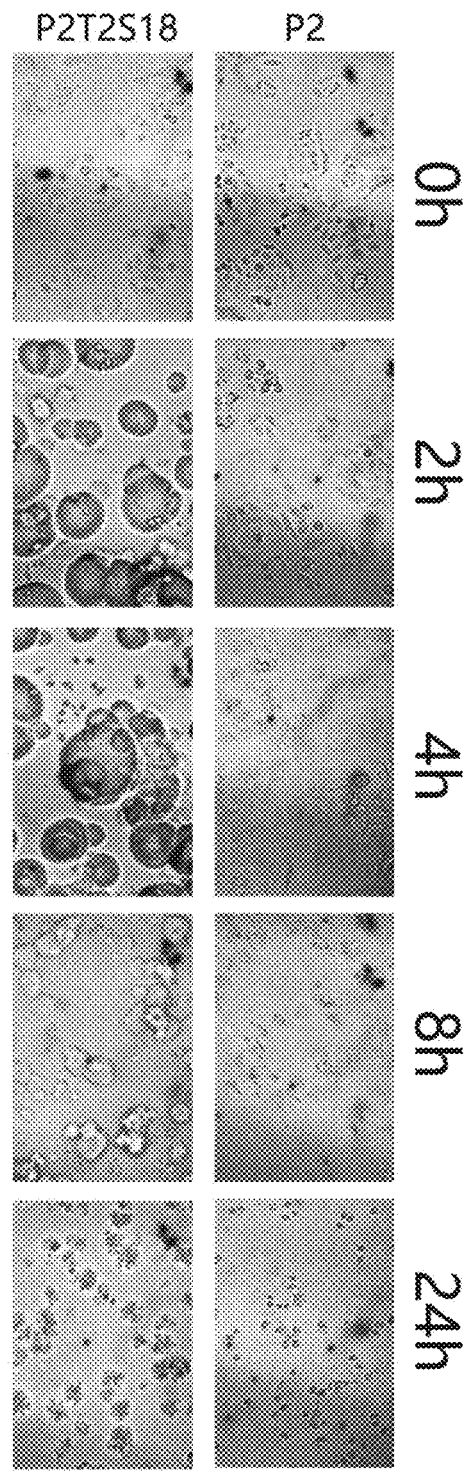
FIG. 6 illustrate that P2T2S18 polypeptide induces in vitro death of SPC-A-1 tumor cell.
Figure 7A:
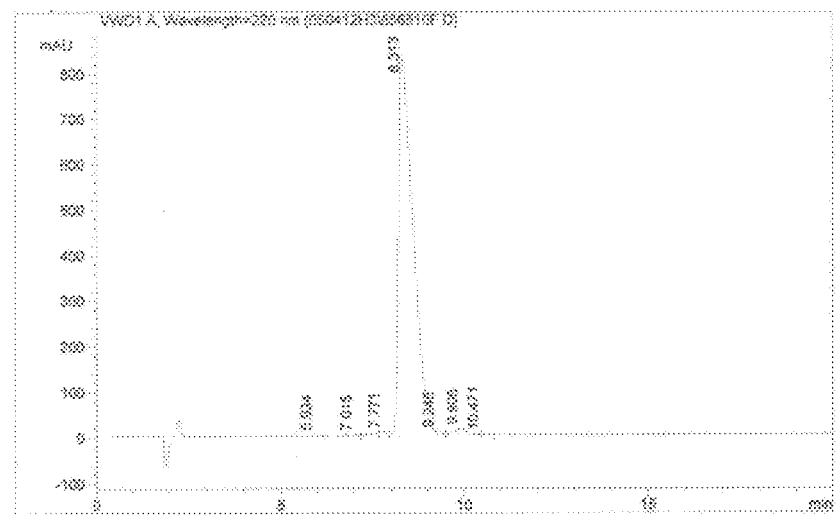
FIGS. 7a and 7b illustrate the HPLC and MASS maps of polypeptide P2T2S18-20, respectively.
Figure 7B:
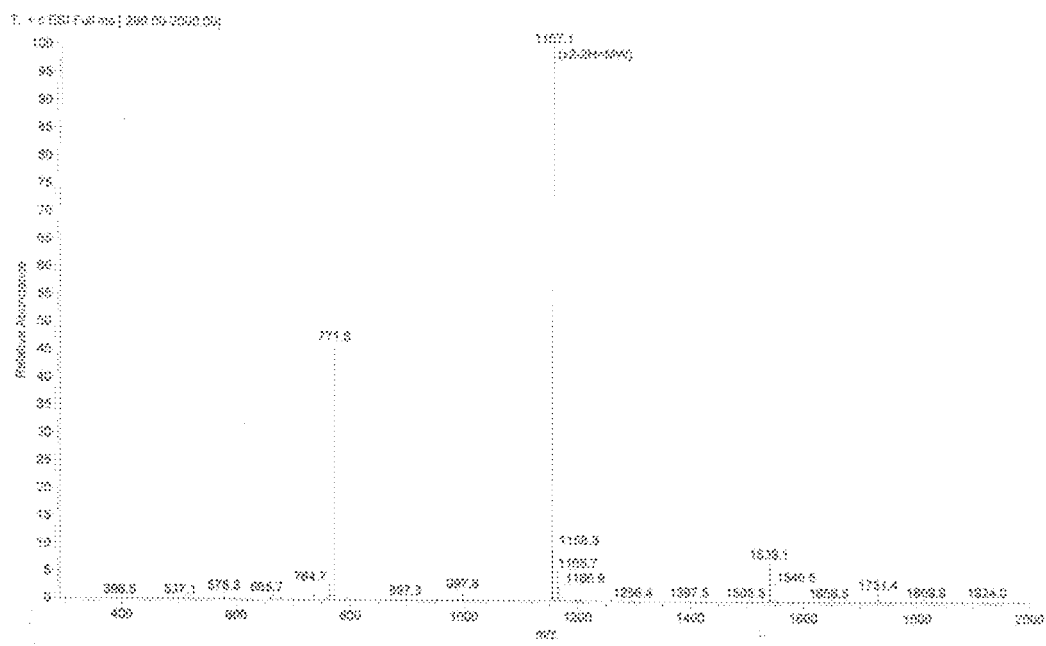
Figure 7C:
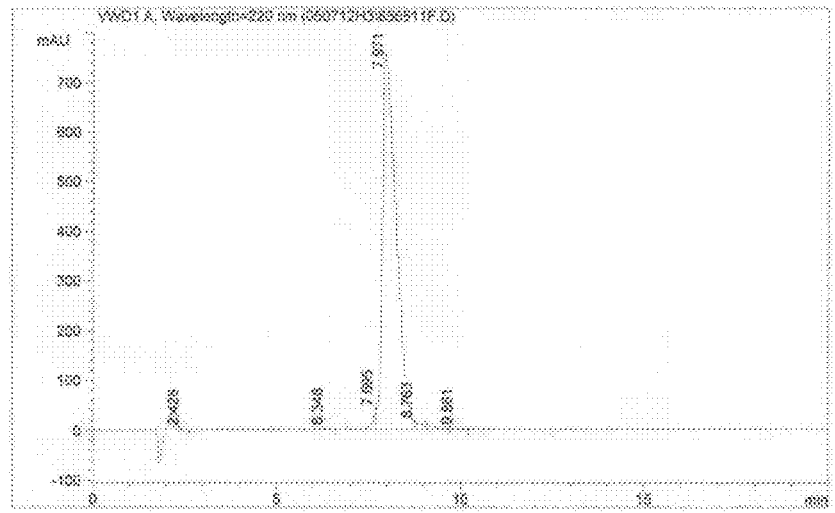
FIGS. 7c and 7d illustrate the HPLC and MASS maps of polypeptide P2T2S18-25, respectively.
Figure 7D:
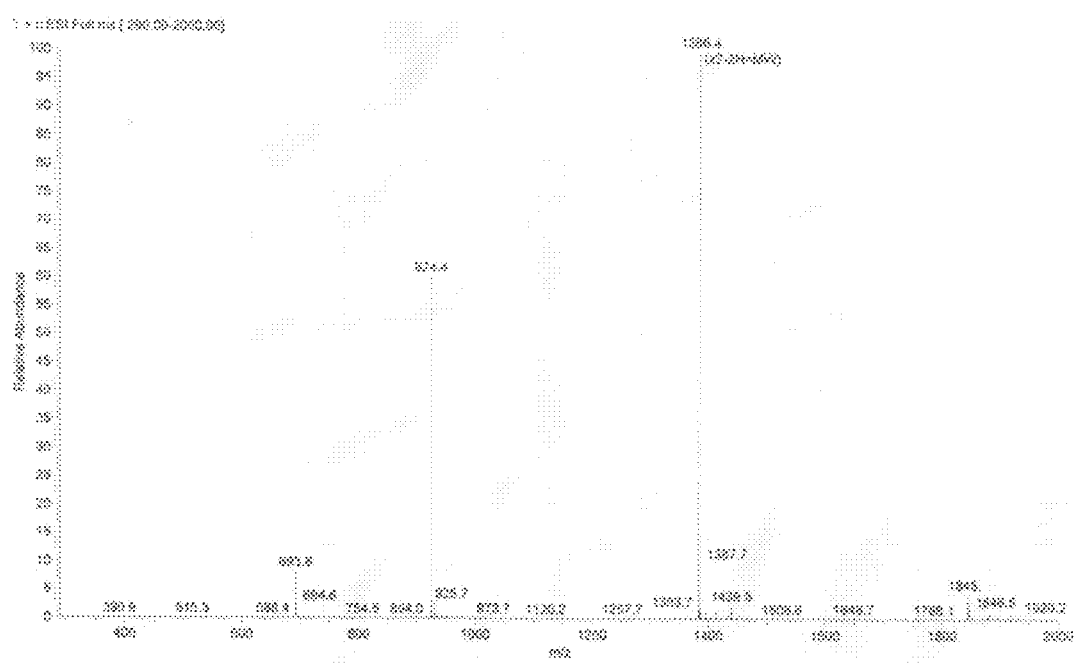
Figure 7E:
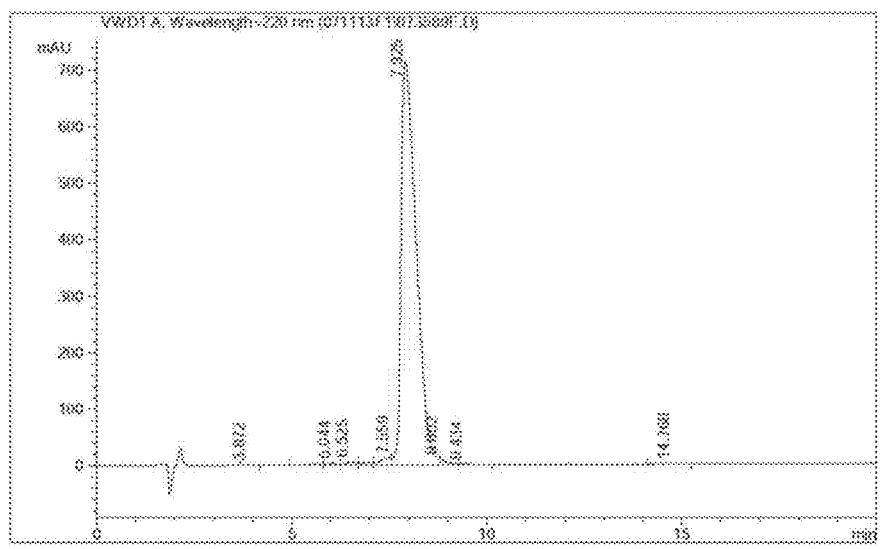
FIGS. 7e and 7f illustrate the HPLC and MASS maps of polypeptide P2T2N18-35, respectively.
Figure 7F:
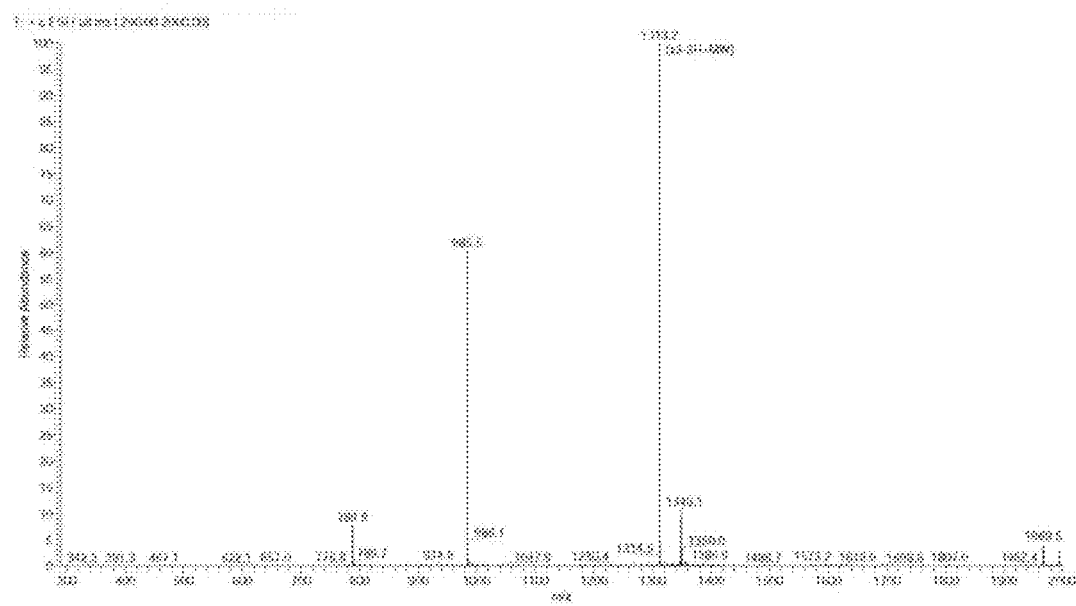
Figure 7G:
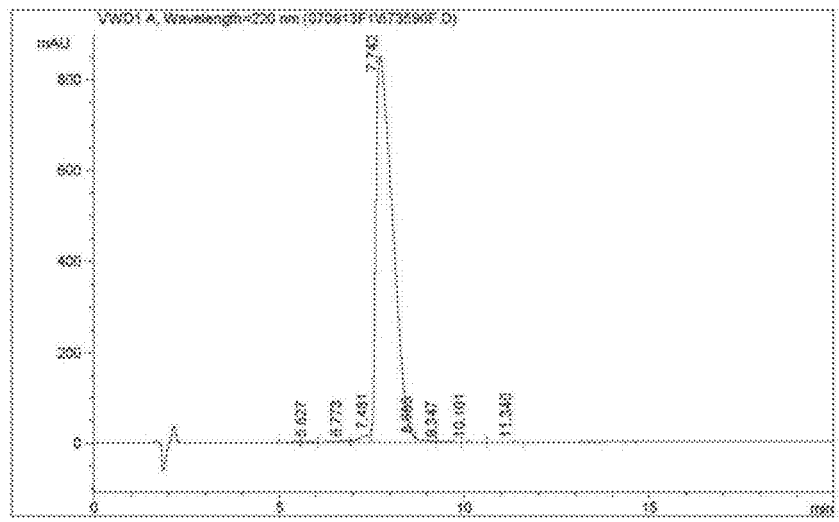
FIGS. 7g and 7h illustrate the HPLC and MASS maps of polypeptide P2T2N18-40, respectively.
Figure 7H:
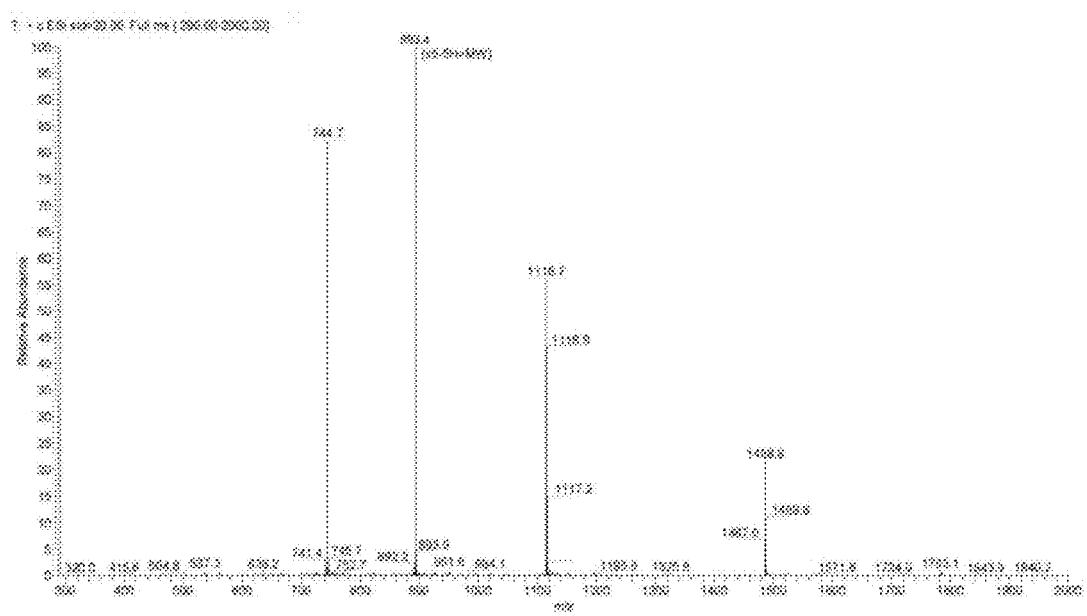
Figure 7I:
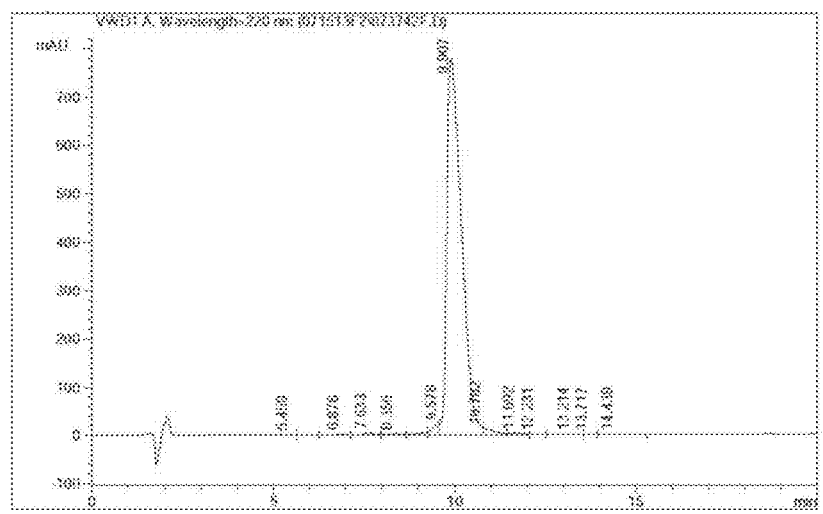
FIGS. 7i and 7j illustrate the HPLC and MASS maps of polypeptide P2T2N18-45, respectively.
Figure 7J:
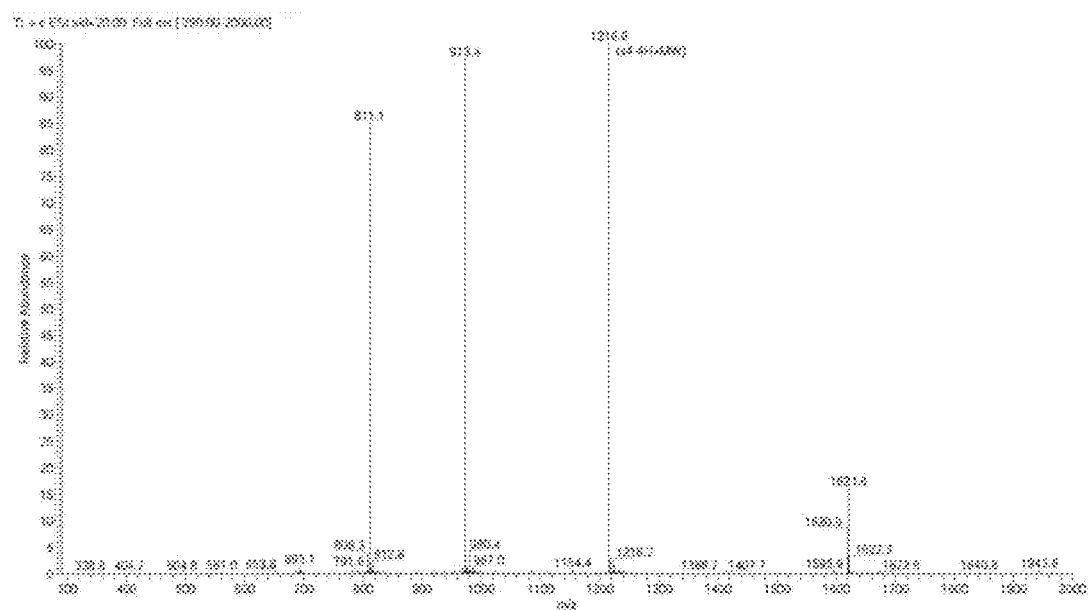

Polypeptides were tested for their effect in inducing cell death of lung cancer cell line SPC-A-1 at a polypeptide concentration of 2.5 mg/ml according to the method described in Example 3. Cells were observed under an optical microscope over 24 hours and photos were taken. Results are shown in FIG. 6. P2 exerts its function 4 hours after being added into the culture medium. Cells shrinked and basically died at 24 hours. The manner of P2 induced cell death is similar to apoptosis. P2T2S18 exhibits violent effect on the cells only 2 hours after added into the culture medium. However, cells did not shrink. On the contrary, they extremely swelled. 4 hours later cells further swelled and began to disintegrate at 8 hours. At 24 hours, only cell debrises left. The manner of P2T2S18 caused cell death is very surprising. Currently, it is unable to determine what manner this kind of cell death belongs to. No report is found in papers as well. However, this mode of cell death is obviously different from that caused by P2. Together with the results in Example 7, it can conclude that P2T2S18 not only has a biological activity obviously higher than P2, but also has a manner causing cell death obviously different from that of P2.

Example 9: Inhibition on In Vitro Growth of HUVEC by Polypeptides

Polypeptides shown in the Table below were synthesized according to the method described in Example 1. Purities were identified by HPLC and molecular weights were identified by MASS spectrometry. Results are shown in FIGS. 1 and 7a-7j.

| No. of Polypeptide | No. of Sequence | Sequence (from N terminus to C terminus) |
|---|---|---|
| P2T2S18-45 | SEQ ID NO: 3 | Ac-HTHRDFQPVLHLVALNSSLSGGMR-GIRGADFQCFQQAR AVGLAGT-NH₂ |
| P2T2S18-40 | SEQ ID NO: 4 | Ac-HTHRDFQPVLHLVALNSSLSGGMRGIRGADFQCFQQAR AV-NH₂ |
| P2T2S18-35 | SEQ ID NO: 5 | Ac-HTHRDFQPVLHLVALNSSLSGGMRGIRGADFQCFQ-NH₂ |
| P2T2S18 | SEQ ID NO: 6 | Ac-HTHRDFQPVLHLVALNSSLSGGMRGIRGAD-NH₂ |
| P2T2S18-25 | SEQ ID NO: 7 | Ac-HTHRDFQPVLHLVALNSSLSGGMRG-NH₂ |
| P2T2S18-20 | SEQ ID NO: 8 | Ac-HTHRDFQPVLHLVALNSSLS-NH₂ |
| P2T2-15 | SEQ ID NO: 24 | Ac-HTHRDFQPVLHLVAL-NH₂ |

Figure 8:
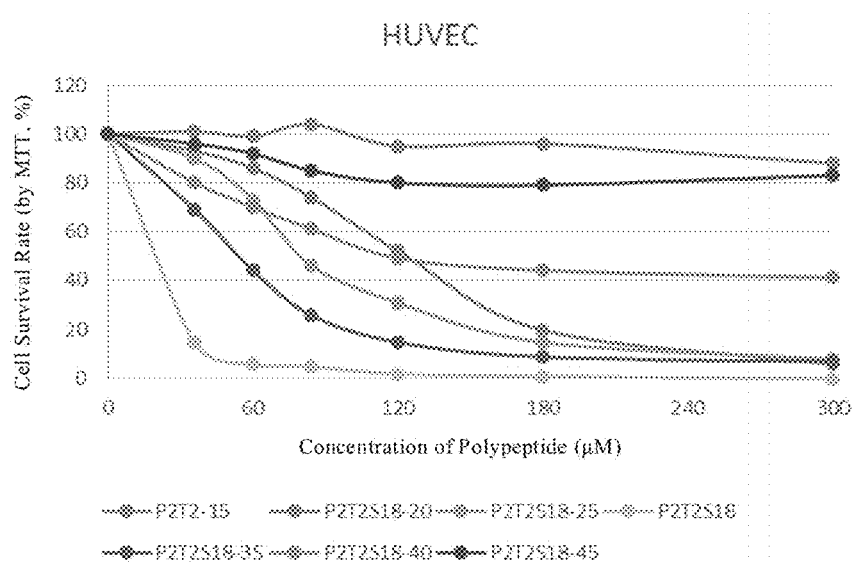
FIG. 8 illustrates the inhibition of polypeptides on in vitro growth of HUVEC. Curves from top to bottom as exemplified at 180 μM concentration respectively show the cell survival rates for P2T2-15, P2T2S18-45, P2T2S18-40, P2T2S18-20, P2T2S18-25, P2T2S18-35 and P2T2S18.

Inhibition of HUVEC by polypeptides was tested according to the method described in Example 3. 300 μM of P2T2S18 corresponds to about 1 mg/ml. Results are shown in FIG. 8 and the following Table, indicating that shortening or extending the C terminus of P2T2S18 by some residues could still maintain the polypeptide biological activity.

| No. of Polypeptide | No. of Sequence | Cell Survival (%) at a polypeptide concentration of 120 μM |
|---|---|---|
| P2T2S18-45 | SEQ ID NO: 3 | 80 |
| P2T2S18-40 | SEQ ID NO: 4 | 49 |
| P2T2S18-35 | SEQ ID NO: 5 | 15 |
| P2T2S18 | SEQ ID NO: 6 | 2 |
| P2T2S18-25 | SEQ ID NO: 7 | 31 |
| P2T2S18-20 | SEQ ID NO: 8 | 52 |
| P2T2-15 | SEQ ID NO: 24 | 95 |

Figure 9:
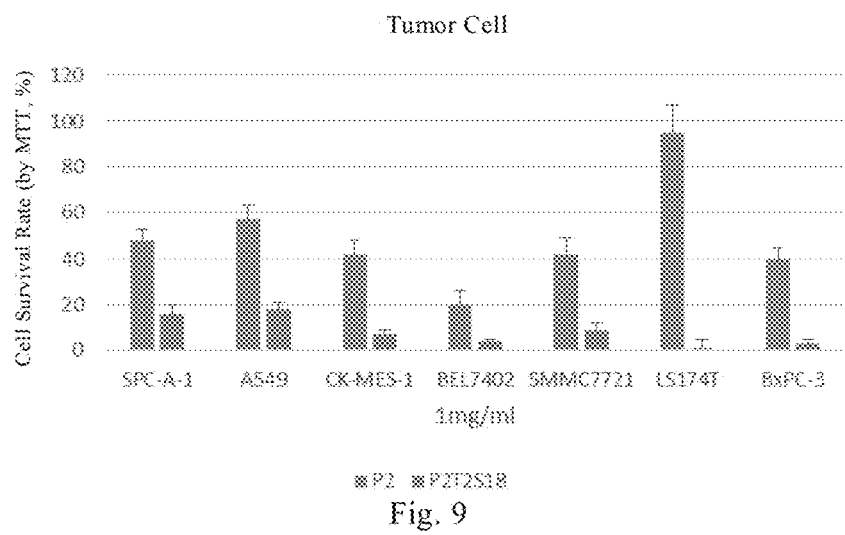
FIG. 9 illustrates in vitro inhibition of the P2T2S18 polypeptide on various tumor cells, SMMC7721, SPC-A-1, A549, LS174T, BEL7402, CK-MES-1 and BxPC-3. For each tumor cell, the left column shows result obtained from P2 and the right column shows the result obtained from P2T2S18.

Example 10: Inhibition on In Vitro Growth of Various Tumor Cells by Polypeptides P2 (SEQ ID NO:2) and P2T2S18 (SEQ ID NO:6) were tested for their in vitro inhibition on SMMC7221, SPC-A-1, A549, LS174T, BEL7402, CK-MES-1 and BxPC-3 at a polypeptide concentration of 1 mg/ml according to the method described in Example 3. Results are shown in FIG. 9 and the following Table. From the results, it can conclude that P2T1S18 exhibit obviously higher inhibition activity on various tumors as compared to P2. All $IC_{50}$ concentrations for P2T2S18 are less than 1/10 $IC_{50}$ concentration of P2. Especially, for the LS174T colon cancer cell, P2 showed no inhibition and cell survival could reach 95% when the drug concentration is 1 mg/ml. On the contrary, P2T2S18 obviously inhibited the cells and almost killed all the tumor cells at the same polypeptide concentration, with only 1% cell survival rate.

| Tumor Cell | Tissue Source | Cell Survival (%) at a polypeptide concentration of 1 mg/ml | | $IC_{50}$ (ug/ml) | |
|---|---|---|---|---|---|
| | | P2 | P2T2S18 | P2 | P2T2S18 |
| SPC-A-1 | lung carcinoma | 48 | 16 | 1111.8 | 80.6 |
| A549 | lung carcinoma | 57 | 18 | 1312.2 | 72.5 |
| CK-MES-1 | lung squamous cell carcinoma | 42 | 7 | 863.1 | 66.7 |
| BEL7402 | Liver cancer | 20 | 4 | 732.9 | 64.9 |
| SMMC7721 | Liver cancer | 42 | 9 | 1030.2 | 76.9 |
| LS174T | Colon cancer | 95 | 1 | 1683.8 | 84.7 |
| BxPC-3 | pancreatic cancer | 40 | 3 | 860.9 | 78.1 |

Figure 10:
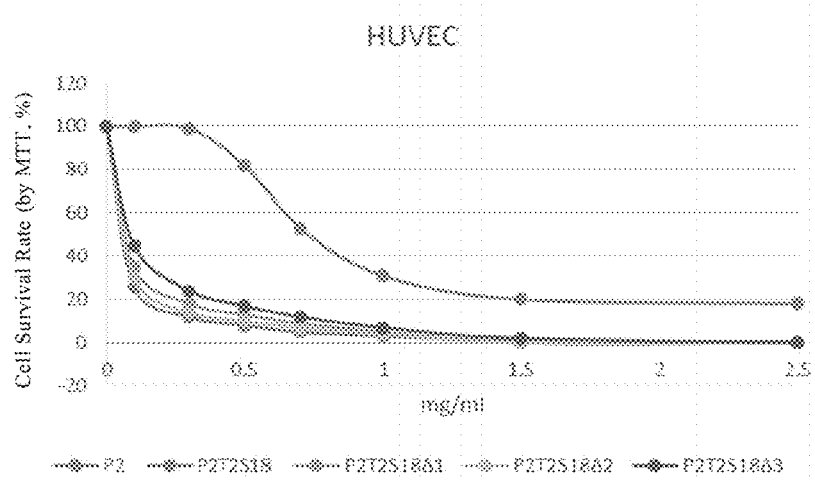
FIG. 10 illustrates in vitro inhibition of polypeptides on HUVEC. Curves from top to bottom as exemplified at the 0.5 mg/ml concentration respectively indicate the cell survival rates for P2, P2T2S18Δ3, P2T2S18Δ1, P2T2S18Δ2 and P2T2S18.

Example 11: Inhibition on In Vitro Growth of Tumor Cells and HUVEC by Polypeptides Polypeptides shown in the Table below were synthesized according to the method described in Example 1. Purities were identified by HPLC and molecular weights were identified by MASS spectrometry. Results are shown in FIGS. 1 and 3a-3f. Inhibition of HUVEC by polypeptides was tested according to the method described in Example 3. Results are shown in FIG. 10.

| No. of Polypeptide | No. of Sequence | Sequence (from N terminus to C terminus) |
|---|---|---|
| P2 | SEQ ID NO: 47 | Ac-HSHRDFQPVLHLVALNSPLSGGMRGIRGAD-NH$_2$ |
| P2T2S18 | SEQ ID NO: 6 | Ac-HTHRDFQPVLHLVALNSSLSGGMRGIRGAD-NH$_2$ |
| P2T2S18Δ1 | SEQ ID NO: 50 | Ac-HTHRDFQPVLHLVALNSSLSGGMRGIRGAD |
| P2T2S18Δ2 | SEQ ID NO: 51 | HTHRDFQPVLHLVALNSSLSGGMRGIRGAD-NH$_2$ |
| P2T2S18Δ3 | SEQ ID NO: 52 | HTHRDFQPVLHLVALNSSLSGGMRGIRGAD |

Example 12: Construction of In Vivo Tumor Model

In vitro cultured tumor cells in exponential phase and in good state were formulated to a 100 μl cell suspension containing 5×10$^6$ tumor cells. The suspension was subcutaneously inoculated to nude mice. Well-grown solid tumors were obtained 15 days later and cut into uniform pieces of about 3 mm under sterile condition. Each nude mouse was inoculated by one piece through a trocar. Mice were re-grouped according the tumor size 10-14 days after inoculation and animals having too large and too small tumor were excluded from the test. The average tumor volume for each group was basically identical. Test drugs were administered to each group according to the experimental protocol. The major axis (a) and minor axis (b) of the tumor were measured twice a week. Animals were sacrificed at the end of the test. The tumor was taken out, weighed and photos were taken. Tumor volume (TV)=½×a×b$^2$; Relative tumor volume (RTV)=Vt/Vo, wherein Vo is the tumor volume measured before grouping (one day before administration of the test drug), and Vt is the tumor volume measured at each time. Tumor inhibition rate (%)=(1−T/C)×100%, wherein T is the average tumor volume of the treatment group and C is the average tumor volume of the negative control group.

Example 13: Inhibition on In Vivo Growth of Tumor Cells by Polypeptides

Polypeptides shown in the Table below were synthesized according to the method described in Example 1. Purities were identified by HPLC and molecular weights were identified by MASS spectrometry. Results are shown in FIG. 1.

| No. of Polypeptide | No. of Sequence | Sequence (from N terminus to C terminus) |
|---|---|---|
| P2 | SEQ ID NO: 47 | Ac-HSHRDFQPVLHLVALNSPLSGGMRGIRGAD-NH$_2$ |
| P2T2S18 | SEQ ID NO: 6 | Ac-HTHRDFQPVLHLVALNSSLSGGMRGIRGAD-NH$_2$ |

Figure 11A:
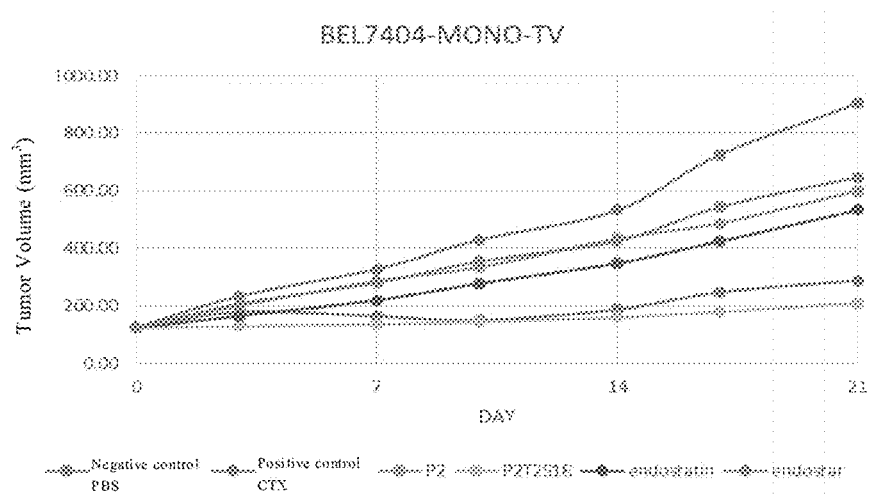
FIGS. 11a and 11b illustrate inhibition on in vivo growth of tumor cell, respectively.
Figure 11B:
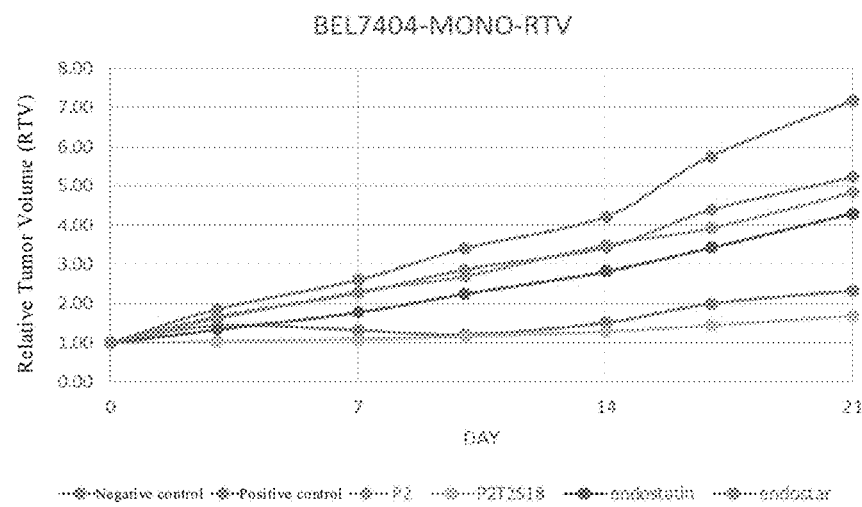

The amino acid sequence of recombination endostatin ("endostatin") was set forth in SEQ ID NO: 1, and the amino acid sequence of the marketed drug Endostar ("endostar") was set forth in SEQ ID NO: 10. Human liver cancer BEL7404 tumor model was constructed according to the method described in Example 10. The test contained 6 groups, with 6 animals in each group, except for the negative control group which contained 9 animals. The molar dose of the polypeptides was basically equal to the molar dose of endostatin. The results are shown in FIGS. 11a and 11b and the following Table.

1) Negative control group (physiological saline, sc, 2 times per day, continuously for 21 days)
2) Cyclophosphamide CTX (30 mg/kg, ip, 1 time per day, continuously for 7 days)
3) P2 group (15 mg/kg/time, sc, 2 times per day, continuously for 21 days)
4) P2T2S18 group (15 mg/kg/time, sc, 2 times per day, continuously for 21 days)
5) endostatin (50 mg/kg/time, sc, 2 times per day, continuously for 21 days)
6) endostar (50 mg/kg/time, sc, 2 times per day, continuously for 21 days)

| Tumor inhibitor rate (%) for each test group | | | | | |
|---|---|---|---|---|---|
| Negative Control | CTX | P2 | P2T2S18 | endostatin | endostar |
| 0 | 68.0 | 33.7 | 76.7 | 41.2 | 28.5 |

RTV between two test groups was subjected to Student's t-test and each p value is shown in the following Table. It can include that P2 could not obviously inhibit increase of tumor and exhibited no significant difference to the negative control group (P=0.015). P2T2S18 could obviously inhibit tumor growth with a tumor inhibition rate of 76.7% 21 days after administration. P2T2S18 even exhibited an inhibition to tumor comparable to the chemotherapeutic agent CTX. No significant difference was present between this two groups (P>0.01). It is noticeable that in the test the P2T2S18 test group did not produce toxic reaction. On the contrary, the CTX group produced a typical chemotherapeutic toxic side effect. For the inhibition effect on tumor, P2T2S18 was obvious superior to P2 (P<0.001), endostatin (P<0.001) and endostar (P<0.001).

| | P value for Student's T test (P < 0.01 indicates significant difference) | | | | | |
|---|---|---|---|---|---|---|
| Test Group | Negative Control | CTX | P2 | P2T2S18 | endostatin | endostar |
| Negative Control | — | <0.001 | 0.015 | <0.001 | 0.0015 | 0.0123 |
| CTX | — | — | 0.001 | 0.05 | 0.002 | <0.001 |
| P2 | — | — | — | <0.001 | 0.217 | 0.6967 |
| P2T2S18 | — | — | — | — | <0.001 | <0.001 |
| endostatin | — | — | — | — | — | 0.0125 |

Example 14: Inhibition on In Vivo Growth of Tumor Cells by Polypeptide in Combination with a Chemotherapeutic Agent Polypeptides shown in the Table below were synthesized according to the method described in Example 1. Purities were identified by HPLC and molecular weights were identified by MASS spectrometry. Results are shown in FIG. 1.

| No. of Polypeptide | No. of Sequence | Sequence (from N terminus to C terminus) |
|---|---|---|
| P2 | SEQ ID NO: 47 | Ac-HSHRDFQPVLHLVALNSPLSGGMRGIRGAD-NH$_2$ |
| P2T2S18 | SEQ ID NO: 6 | Ac-HTHRDFQPVLHLVALNSSLSGGMRGIRGAD-NH$_2$ |

The amino acid sequence of recombination endostatin ("endostatin") was set forth in SEQ ID NO: 1, and the amino acid sequence of the marketed drug Endostar ("endostar") was set forth in SEQ ID NO: 10. Human lung cancer A549 tumor model was constructed according to the method described in Example 10. The test contained 7 groups, with 6 animals in each group. The molar dose of the polypeptides was basically equal to the molar dose of endostatin.

1) Negative control group: physiological saline, sc, 2 times per day, continuously for 21 days;
2) Cisplatin (DDP) group (low dose): 2 mg/kg/day, ip, 1 time per day, continuously for 7 days;
3) P2+DDP group:
   DDP: 2 mg/kg/day, ip, 1 time per day, continuously for 7 days,
   P2: 15 mg/kg/time, sc, 2 times per day, continuously for 21 days;
4) P2T2S18+DDP group:
   DDP: 2 mg/kg/day, ip, 1 time per day, continuously for 7 days,
   P2T2S18: 15 mg/kg/time, sc, 2 times per day, continuously for 21 days;

5) Recombination endostatin (SEQ ID NO: 1)+DDP group:
DDP: 2 mg/kg/day, ip, 1 time per day, continuously for 7 days,
Endostatin: 50 mg/kg/time, sc, 2 times per day, continuously for 21 days;
6) Recombination endostatin (SEQ ID NO: 10)+DDP group
DDP: 2 mg/kg/day, ip, 1 time per day, continuously for 7 days,
Endostar: 50 mg/kg/time, sc, 2 times per day, continuously for 21 days;
7) DDP group (high dose): 6 mg/kg/day, ip, 1 time per day, continuously for 7 days.

Figure 12A:
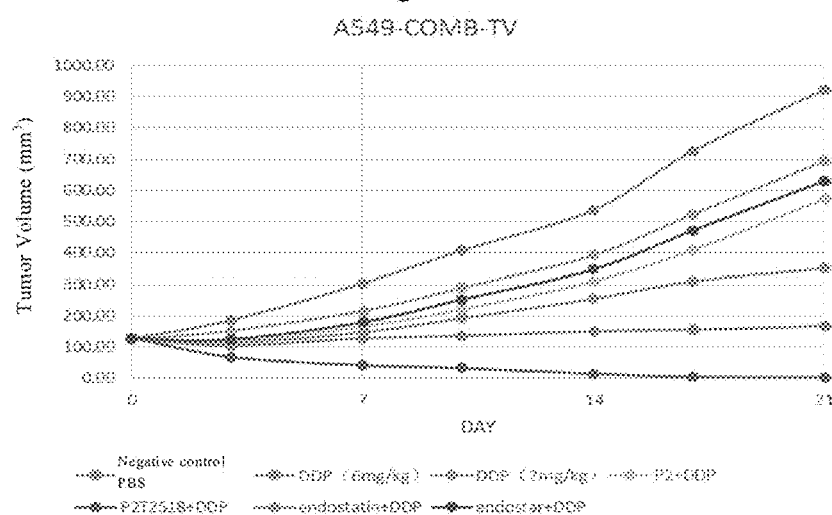
FIGS. 12a and 12b illustrate the inhibition of polypeptides in combination with a chemotherapeutic agent on in vivo growth of tumor cell, respectively.
Figure 12B:
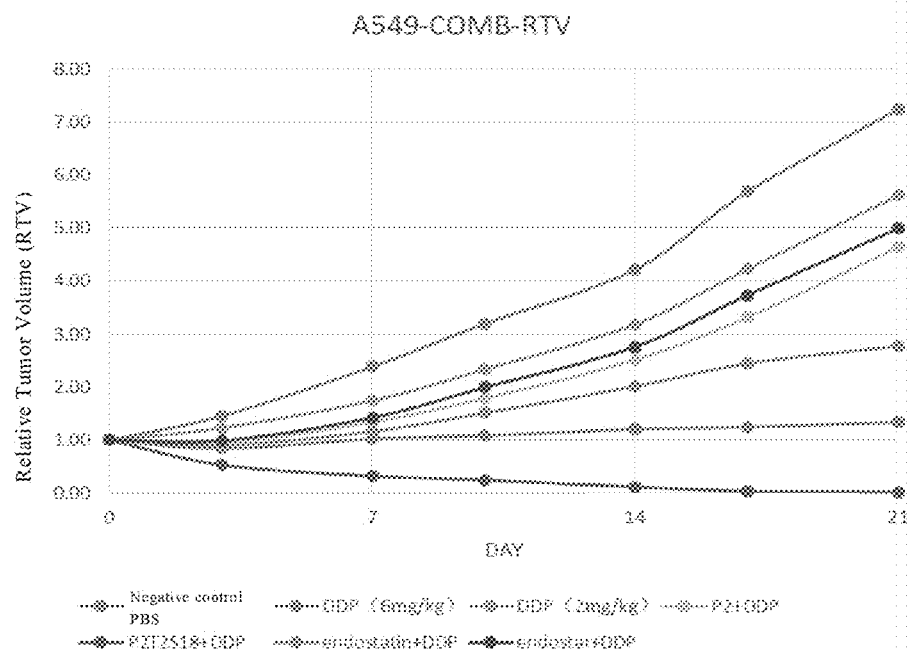

Results are shown in FIGS. 12a and 12b and the following Table.

| | | | Tumor inhibitor rate (%) for each test group | | | |
|---|---|---|---|---|---|---|
| Negative control | DDP 2 mg | P2 + DDP | P2T2S18 + DDP | Endostatin + DDP | Endostar + DDP | DDP 6 mg |
| 0 | 24.8 | 38.0 | 99.7 | 61.9 | 31.7 | 81.9 |

RTV between two test groups was subjected to Student's t-test and each p value is shown in the following Table. It can conclude that P2 in combination with DDP (2 mg/kg) could not obviously increase the tumor inhibition induced by DDP (2 mg/kg). The RTV of these two test groups are not significantly different (P=0.11). Inhibition on tumor produced by P2 in combination with DDP (2 mg/kg) is obviously inferior to DDP (6 mg/kg). The RTV of these two test groups exhibited a significant difference (P<0.001). P2T2S18 could obviously improve the tumor inhibition induced by DDP (2 mg/kg). Inhibition on tumor produced by P2T2S18 in combination with DDP (2 mg/kg) was obviously superior to DDP (2 mg/kg). The RTV of these two test groups was significantly different (P<0.001). Inhibition on tumor produced by P2T2S18 in combination with DDP (2 mg/kg) was even obviously superior to DDP (5 mg/kg), with a tumor inhibition rate of up to 99.7% 21 days after administration. And in the P2T2S18+DDP (2 mg/kg) group, only 2 in the 6 animals had residual tumor, while tumors in all other 4 animals disappeared. On the contrary, in the DDP (6 mg/kg) group, all 6 animals had residual tumor. The RTV from the P2T2S18+DDP (2 mg/kg) group was smaller than the DDP (6 mg/kg) group, and the difference was significant (P<0.001). Thus, P2T2S18 in combination with DDP (2 mg/kg) had an efficacy superior to DDP (6 mg/kg).

Efficacy of the P2T2S18+DDP (2 mg/kg) group was also superior to the efficacy of the P2+DDP (2 mg/kg) group (P<0.001), the endostatin+DDP (2 mg/kg) group (P<0.001) and the endostar+DDP (2 mg/kg) group (P<0.001).

It is noticeable that in the test no obvious toxic reaction was observed in the P2T2S18+DDP (2 mg/kg) group and the DDP (2 mg/kg) groups. On the contrary, the DDP (6 mg/kg) group produced obvious chemotherapeutic toxic side effect.

| | P value for Student's T test ($P < 0.01$ indicates significant difference) | | | | | |
|---|---|---|---|---|---|---|
| Test Group | DDP 2 mg | P2 + DDP | P2T2S18 + DDP | Endostatin + DDP | Endostar + DDP | DDP 6 mg |
| Negative Control | <0.001 | <0.001 | <0.001 | <0.001 | <0.001 | <0.001 |
| DDP 2 mg | | 0.011 | <0.001 | <0.001 | 0.159 | <0.001 |
| P2 + DDP | — | — | <0.001 | <0.001 | 0.209 | <0.001 |
| P2T2S18 + DDP | — | — | — | <0.001 | <0.001 | <0.001 |
| Endostatin + DDP | — | — | — | — | <0.001 | <0.001 |
| Endostar + DDP | — | — | — | — | — | <0.001 |

Figure 13:
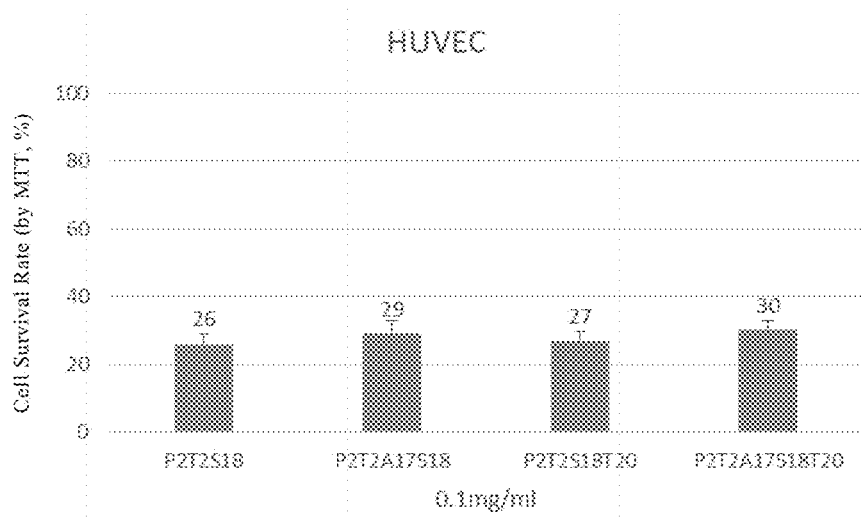
FIG. 13 shows inhibition of polypeptides on in vitro growth of HUVEC.

Example 15: Inhibition on In Vitro Growth of Tumor Cells and HUVEC by Polypeptides Polypeptides shown in the Table below were synthesized according to the method described in Example 1. Inhibition of HUVEC by polypeptides at a polypeptide concentration of 0.1 mg/ml was tested according to the method described in Example 3. Results are shown in FIG. 13.

| No. of Polypeptide | No. of Sequence | Sequence (from N terminus to C terminus) |
|---|---|---|
| P2T2S18 | SEQ ID NO: 6 | Ac-H<u>T</u>HRDFQPVLHLVALNS<u>S</u>LSGGMRGIRGAD-NH$_2$ |
| P2T2A17S18 | SEQ ID NO: 27 | Ac-H<u>T</u>HRDFQPVLHLVALN<u>AS</u>LSGGMRGIRGAD-NH$_2$ |
| P2T2S18T20 | SEQ ID NO: 28 | Ac-H<u>T</u>HRDFQPVLHLVALNS<u>SLT</u>GGMRGIRGAD-NH$_2$ |
| P2T2A17S18T20 | SEQ ID NO: 29 | Ac-H<u>T</u>HRDFQPVLHLVALN<u>AS</u>L<u>T</u>GGMRGIRGAD-NH$_2$ |

Figure 14A:
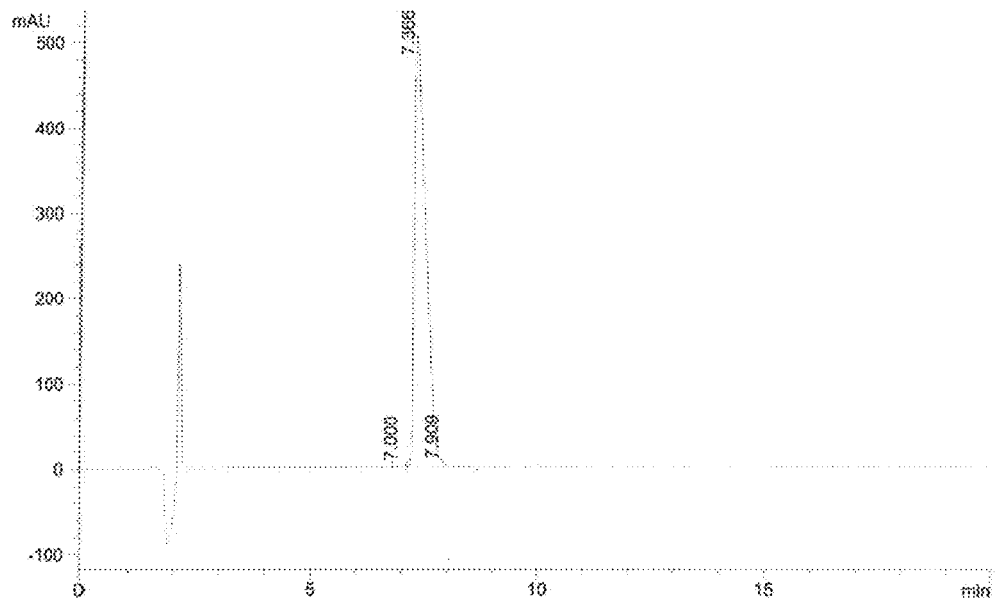
FIGS. 14a and 14b illustrate the HPLC and MASS maps of polypeptide P2T2S18-29, respectively.
Figure 14B:
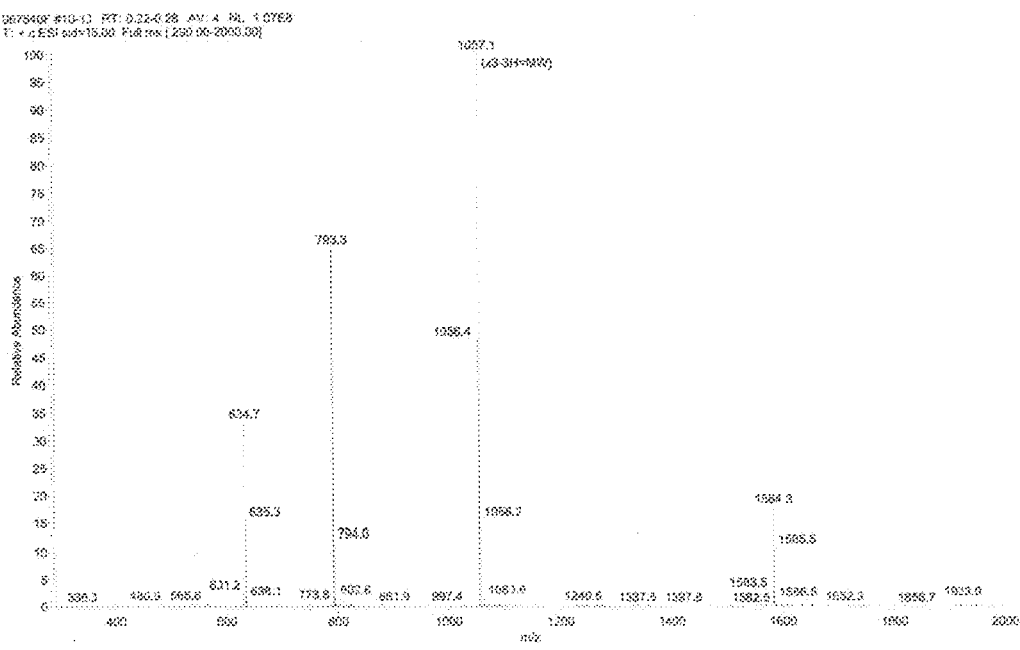
Figure 15:
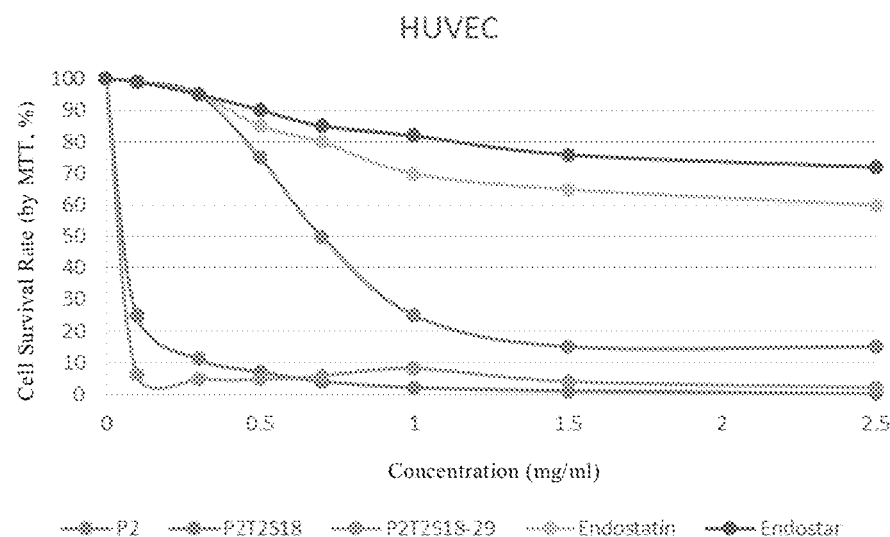
FIG. 15 illustrates inhibition of P2T2S18-29 on HUVEC. Curves from top to bottom as exemplified at the 2.5 mg/ml concentration respectively indicate the cell survival rates for Endostar, Endostatin, P2, P2T2S18-29 and P2T2S18.
Figure 16:
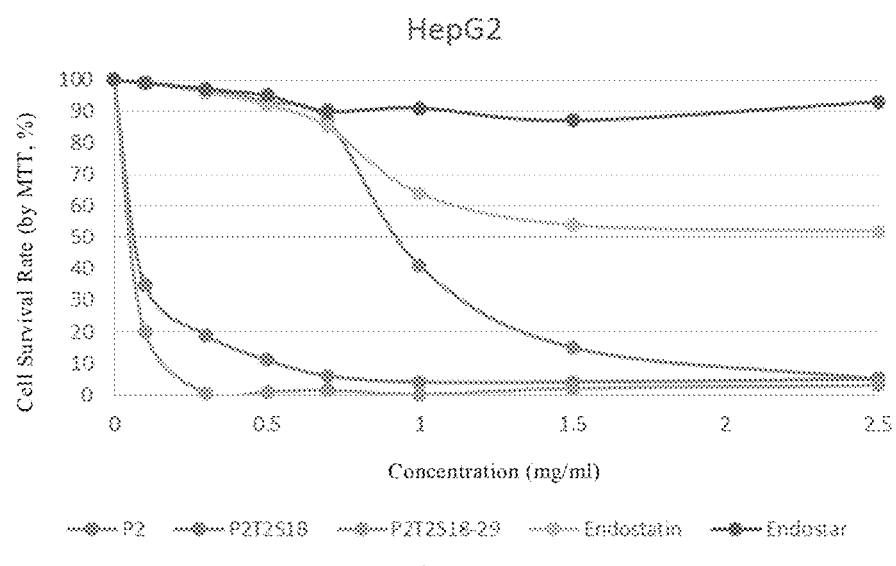
FIG. 16 illustrates inhibition of P2T2S18-29 on HepG2. Curves from top to bottom as exemplified at the 1.0 mg/ml concentration respectively indicate the cell survival rates for Endostar, Endostatin, P2, P2T2S18 and P2T2S18-29.

Example 16: Inhibition on In Vitro Growth of Tumor Cells and HUVEC by Polypeptides Polypeptides shown in the Table below were synthesized according to the method described in Example 1. Purities were identified by HPLC and molecular weights were identified by MASS spectrometry. Results are shown in FIGS. 14a and 14b. Inhibition of HUVEC and tumore cell HepG2 by polypeptides was tested according to the method described in Example 3. Results are shown in FIGS. 15 and 16. Results show that P2T2S18 and P2T2S19-29 exhibit a similar biological activity. Both are siginficalty higher than P2.

| No. of Polypeptide | No. of Sequence | Sequence (from N terminus to C terminus) |
|---|---|---|
| P2T2S18-29 | SEQ ID NO: 41 | Ac-HTHRDFQPVLHLVALNSSLSGGMR GIRGA-NH$_2$ |

The above specific Examples are merely for illustrative purpose, but not for limiting purpose. The protection scope of the subject application should be defined by the claims. It should be understood by the skilled artisan that various modifications and changes could be made to the technical solutions of the present disclosure without departing from the spirit and scope of the subject disclosure, all of which are still included in the scope of the present disclosure.

---

The invention claimed is:

1. A polypeptide, wherein the polypeptide is a fragment of the N terminus of endostatin, has 45 or fewer amino acid residues, and contains at least amino acid residues 1 to 20 of the N terminus, and wherein the amino acid residues at positions 2 and 18 of the N terminus of endostatin are respectively selected from the combinations as shown below:

| Amino acid residue at position 2 | Amino acid residue at position 18 |
|---|---|
| A | M |
| R | I |
| N | K |
| D | E, M, T or Y |
| Q | A or H |
| E | S or V |
| H | A or S |
| L | R, E or S |
| K | V |
| M | L or W |
| F | T |
| P | C or V |
| T | N, G, K, M, F, S or T |
| W | C, E, I, K, S or Y |
| Y | R, H, W or V |
| V | D or S. |

-continued

| Amino acid residue at position 2 | Amino acid residue at position 18 |
|---|---|

2. The polypeptide of claim 1, wherein the polypeptide contains at least amino acid residues 1-22 of SEQ ID NO: 38, and the amino acid residues at positions 2 and 18 are defined as in claim 1.

3. The polypeptide of claim 1, wherein:
the polypeptide contains at least amino acid residues 1-22 of SEQ ID NO: 38, or at least amino acid residues 1-25 of SEQ ID NO: 38, and the amino acid residue at position 2 is T, the amino acid residue at position 18 is N, G, K, M, F, S or T, and the amino acid residues at positions 17, 20, 21 and 22 are defined as in claim 1; or
the polypeptide contains at least amino acid residues 1-22 of SEQ ID NO: 38, or at least amino acid residues 1-25 of SEQ ID NO: 38, and the amino acid residue at position 18 is N, the amino acid residue at position 2 is T, and the amino acid residues at positions 17, 20, 21 and 22 are defined as in claim 1; or
the polypeptide contains at least amino acid residues 1-22 of SEQ ID NO: 38, or at least amino acid residues 1-25 of SEQ ID NO: 38, and the amino acid residue at position 18 is S, the amino acid residue at position 2 is E, H, L, T, W or V, and the amino acid residues at positions 17, 20, 21 and 22 are defined as in claim 1; or
the amino acid sequence of the polypeptide is set forth in any of SEQ ID NOs: 4, 5, 6, 7, 27-30, 39 and 41; or
the polypeptide consists of SEQ ID NO: 38, wherein the amino acid residue at position 2 is T, the amino acid residue at position 18 is N or S, and the amino acid residues at positions 17, 20, 21 and 22 are defined as in claim 1; or
the polypeptide is selected from the group of amino acid sequences consisting of amino acid residue 1 to residue 39, 38, 37, 36, 34, 33, 32, 31, 29, 28, 27 and 26 of SEQ ID NO: 4, or selected from the group of amino acid sequences consisting of amino acid residue 1 to amino acid residue 39, 38, 37, 36, 35, 34, 33, 32, 31, 29, 28, 27, 26 and 25 of SEQ ID NO: 39; and/or
the first amino acid residue in the N terminus of the polypeptide is histidine, which is modified by formylation, acetylation, propionylation or butyrylation, and the C-terminal amino acid may be modified by PEG, cholesterol or amidation.

4. The polypeptide of claim 1, wherein the polypeptide is selected from the group consisting of:

```
                                    (SEQ ID NO: 52)
HTHRDFQPVLHLVALNSSLSGGMRGIRGAD;

(SEQ ID NO: 50)
Ac-HTHRDFQPVLHLVALNSSLSGGMRGIRGAD;

(SEQ ID NO: 51)
HTHRDFQPVLHLVALNSSLSGGMRGIRGAD-NH2;

(SEQ ID NO: 6)
Ac-HTHRDFQPVLHLVALNSSLSGGMRGIRGAD-NH2;

(SEQ ID NO: 7)
Ac-HTHRDFQPVLHLVALNSSLSGGMRG-NH2;

(SEQ ID NO: 5)
Ac-HTHRDFQPVLHLVALNSSLSGGMRGIRGADFQCFQ-NH2;

(SEQ ID NO: 4)
Ac-HTHRDFQPVLHLVALNSSLSGGMRGIRGADFQCFQQARAV-NH2;

(SEQ ID NO: 53)
HTHRDFQPVLHLVALNSNLSGGMRGIRGAD;

(SEQ ID NO: 54)
Ac-HTHRDFQPVLHLVALNSNLSGGMRGIRGAD;

(SEQ ID NO: 55)
HTHRDFQPVLHLVALNSNLSGGMRGIRGAD-NH2;

(SEQ ID NO: 9)
Ac-HTHRDFQPVLHLVALNSNLSGGMRGIRGAD-NH2;

(SEQ ID NO: 27)
Ac-HTHRDFQPVLHLVALNASLSGGMRGIRGAD-NH2;

(SEQ ID NO: 28)
Ac-HTHRDFQPVLHLVALNSSLTGGMRGIRGAD-NH2;

(SEQ ID NO: 29)
Ac-HTHRDFQPVLHLVALNASLTGGMRGIRGAD-NH2;
and
                                    (SEQ ID NO: 41)
Ac-HTHRDFQPVLHLVALNSSLSGGMRGIRGA-NH2;
``` wherein Ac represents acetylation modification, and NH2 represent amidation modification.

5. The polypeptide of claim 1, wherein the amino acid residue at position 17 of the N terminus of endostatin is S, A, L, I or T; and/or the amino acid residue at position 20 is S or T; and/or, if present, the amino acid residue at position 21 is S or T; and/or, if present, the amino acid residue at position 22 is G, A, L, I or V.

6. The polypeptide of claim 1, wherein the amino acid sequence of the endostatin is set forth in SEQ ID NO: 1.

7. The polypeptide of claim 1, wherein the polypeptide contains at least amino acid residues 1-25 of SEQ ID NO: 38, and amino acid residues at positions 2 and 18 are defined as in claim 1.

8. A pharmaceutical composition, comprising the polypeptide of claim 1 and a pharmaceutically acceptable carrier.

9. The pharmaceutical composition of claim 8, wherein the polypeptide is:
a polypeptide containing at least amino acid residues 1-22 of SEQ ID NO: 38, or at least amino acid residues 1-25 of SEQ ID NO: 38, wherein the amino acid residue at position 2 is T, and the amino acid residue at position 18 is N, G, K, M, F, S or T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide containing at least amino acid residues 1-22 of SEQ ID NO: 38, or at least amino acid residues 1-25 of SEQ ID NO: 38, wherein the amino acid residue at position 18 is N, and the amino acid residue at position 2 is T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide containing at least amino acid residues 1-22 of SEQ ID NO: 38, or at least amino acid residues 1-25 of SEQ ID NO: 38, wherein the amino acid residue at position 18 is S, and the amino acid residue at position 2 is E, H, L, T, W or V; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or a polypeptide set forth in any of SEQ ID NO: 4, 5, 6, 7, 27-30, 39 and 41; or a polypeptide consisting of SEQ ID NO: 38, wherein the amino acid residue at position 2 is T, and the amino acid residue at position 18 is N or S; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or a polypeptide selected from the group amino acid sequences consisting of amino acid residue 1 to residue 39, 38, 37, 36, 34, 33, 32, 31, 29, 28, 27 and 26 of SEQ ID NO: 4, or selected from the group amino acid sequences consisting of amino acid residue 1 to amino acid residue 39, 38, 37, 36, 35, 34, 33, 32, 31, 29, 28, 27, 26 and 25 of SEQ ID NO: 39.

10. The pharmaceutical composition of claim 8, wherein the polypeptide is selected from the group consisting of:

```
                                                (SEQ ID NO: 52)
HTHRDFQPVLHLVALNSSLSGGMRGIRGAD;

(SEQ ID NO: 50)
Ac-HTHRDFQPVLHLVALNSSLSGGMRGIRGAD;

(SEQ ID NO: 51)
HTHRDFQPVLHLVALNSSLSGGMRGIRGAD-NH2;

(SEQ ID NO: 6)
Ac-HTHRDFQPVLHLVALNSSLSGGMRGIRGAD-NH2;

(SEQ ID NO: 7)
Ac-HTHRDFQPVLHLVALNSSLSGGMRG-NH2;

(SEQ ID NO: 5)
Ac-HTHRDFQPVLHLVALNSSLSGGMRGIRGADFQCFQ-NH2;

(SEQ ID NO: 4)
Ac-HTHRDFQPVLHLVALNSSLSGGMRGIRGADFQCFQQARAV-NH2;

(SEQ ID NO: 53)
HTHRDFQPVLHLVALNSNLSGGMRGIRGAD;

(SEQ ID NO: 54)
Ac-HTHRDFQPVLHLVALNSNLSGGMRGIRGAD;

(SEQ ID NO: 55)
HTHRDFQPVLHLVALNSNLSGGMRGIRGAD-NH2;

(SEQ ID NO: 9)
Ac-HTHRDFQPVLHLVALNSNLSGGMRGIRGAD-NH2;

(SEQ ID NO: 27)
Ac-HTHRDFQPVLHLVALNASLSGGMRGIRGAD-NH2;

(SEQ ID NO: 28)
Ac-HTHRDFQPVLHLVALNSSLTGGMRGIRGAD-NH2;

(SEQ ID NO: 29)
Ac-HTHRDFQPVLHLVALNASLTGGMRGIRGAD-NH2;
and
                                                (SEQ ID NO: 41)
Ac-HTHRDFQPVLHLVALNSSLSGGMRGIRGA-NH2.
```

11. A method for treating or preventing tumor or for improving the efficacy of a chemotherapy agent, comprising administering the polypeptide of claim 1 or a pharmaceutical composition thereof to a subject in need thereof.

12. The method of claim 11, wherein:
(1) the tumor is selected from the group consisting of: lung carcinoma, lung squamous cell carcinoma, liver cancer, color cancer, pancreatic cancer, rhabdomyosarcoma, retinoblastoma, Ewing sarcoma, neuroblastoma and osteosarcoma; and
(2) the chemotherapy agent is cisplatin, carboplatin or oxaliplatin.

13. A polynucleotide sequence, selected from the group consisting of:
(1) a polynucleotide sequence encoding any of the polypeptides of claim 1; and
(2) a polynucleotide sequence complementary to any of the polynucleotide sequences of (1).

14. The polynucleotide sequence of claim 13, wherein the polynucleotide sequence is selected from the group consisting of:
(1) SEQ ID NO:32, 33, 34, 35, 37 and 40;
(2) polynucleotides consisting of base 1 to base 117, 114, 111, 108, 102, 99, 96, 93, 87, 84, 81 or 78 of SEQ ID NO: 32; and
(3) polynucleotides consisting of base 1 to base 117, 114, 111, 108, 105, 102, 99, 96, 93, 87, 84, 81, 78 or 75 of SEQ ID NO: 40.

15. The polynucleotide sequence of claim 13, selected from the group consisting of:
(1) a polynucleotide sequence encoding any of the following polypeptides:

a polypeptide containing at least amino acid residues 1-22 of SEQ ID NO: 38, or at least amino acid residues 1-25 of SEQ ID NO: 38, wherein the amino acid residue at position 2 is T, and the amino acid residue at position 18 is N, G, K, M, F, S or T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or a polypeptide containing at least amino acid residues 1-22 of SEQ ID NO: 38, or at least amino acid residues 1-25 of SEQ ID NO: 38, wherein the amino acid residue at position 18 is N, and the amino acid residue at position 2 is T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or a polypeptide containing at least amino acid residues 1-22 of SEQ ID NO: 38, or at least amino acid residues 1-25 of SEQ ID NO: 38, wherein the amino acid residue at position 18 is S, and the amino acid residue at position 2 is E, H, L, T, W or V; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or a polypeptide set forth in any of SEQ ID NOs: 4, 5, 6, 7, 27-30, 39 and 41; or a polypeptide consisting of SEQ ID NO: 38, wherein the amino acid residue at position 2 is T, and the amino acid residue at position 18 is N or S; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide selected from the group amino acid sequences consisting of amino acid residue 1 to residue 39, 38, 37, 36, 34, 33, 32, 31, 29, 28, 27 and 26 of SEQ ID NO: 4, or selected from the group amino acid sequences consisting of amino acid residue 1 to amino acid residue 39, 38, 37, 36, 35, 34, 33, 32, 31, 29, 28, 27, 26 and 25 of SEQ ID NO: 39; and
(2) a polynucleotide sequence complementary to any of the polynucleotide sequences of (1).

16. The polynucleotide sequence of claim 15, selected from the group consisting of:
(1) a polynucleotide sequence encoding a polypeptide selected from the group consisting of:

```
                                              (SEQ ID NO: 52)
HTHRDFQPVLHLVALNSSLSGGMRGIRGAD;

(SEQ ID NO: 50)
Ac-HTHRDFQPVLHLVALNSSLSGGMRGIRGAD;

(SEQ ID NO: 51)
HTHRDFQPVLHLVALNSSLSGGMRGIRGAD-NH2;

(SEQ ID NO: 6)
Ac-HTHRDFQPVLHLVALNSSLSGGMRGIRGAD-NH2;

(SEQ ID NO: 7)
Ac-HTHRDFQPVLHLVALNSSLSGGMRG-NH2;

(SEQ ID NO: 5)
Ac-HTHRDFQPVLHLVALNSSLSGGMRGIRGADFQCFQ-NH2;

(SEQ ID NO: 4)
Ac-HTHRDFQPVLHLVALNSSLSGGMRGIRGADFQCFQQARAV-NH2;

(SEQ ID NO: 53)
HTHRDFQPVLHLVALNSNLSGGMRGIRGAD;

(SEQ ID NO: 54)
Ac-HTHRDFQPVLHLVALNSNLSGGMRGIRGAD;

(SEQ ID NO: 55)
HTHRDFQPVLHLVALNSNLSGGMRGIRGAD-NH2;

(SEQ ID NO: 9)
Ac-HTHRDFQPVLHLVALNSNLSGGMRGIRGAD-NH2;

(SEQ ID NO: 27)
Ac-HTHRDFQPVLHLVALNASLSGGMRGIRGAD-NH2;

(SEQ ID NO: 28)
Ac-HTHRDFQPVLHLVALNSSLTGGMRGIRGAD-NH2;

(SEQ ID NO: 29)
Ac-HTHRDFQPVLHLVALNASLTGGMRGIRGAD-NH2;
and (SEQ ID NO: 41)
Ac-HTHRDFQPVLHLVALNSSLSGGMRGIRGA-NH2;
```

(2) a sequence complementary to any of the polynucleotide sequences of (1).

17. An expression vector, containing the polynucleotide of claim 13.

18. The expression vector of claim 17, wherein the polynucleotide sequence is selected from the group consisting of:
(1) SEQ ID NO:32, 33, 34, 35, 37 and 40;
(2) polynucleotides consisting of base 1 to base 117, 114, 111, 108, 102, 99, 96, 93, 87, 84, 81 or 78 of SEQ ID NO: 32; and
(3) polynucleotides consisting of base 1 to base 117, 114, 111, 108, 105, 102, 99, 96, 93, 87, 84, 81, 78 or 75 of SEQ ID NO: 40.

19. The expression vector of claim 17, wherein the polynucleotide sequence is selected from the group consisting of:
(1) a polynucleotide sequence encoding any of the following polypeptides:
a polypeptide containing at least amino acid residues 1-22 of SEQ ID NO: 38, preferably at least amino acid residues 1-25 of SEQ ID NO: 38, wherein the amino acid residue at position 2 is T, and the amino acid residue at position 18 is N, G, K, M, F, S or T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide containing at least amino acid residues 1-22 of SEQ ID NO: 38, preferably at least amino acid residues 1-25 of SEQ ID NO: 38, wherein the amino acid residue at position 18 is N, and the amino acid residue at position 2 is T; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide containing at least amino acid residues 1-22 of SEQ ID NO: 38, preferably at least amino acid residues 1-25 of SEQ ID NO: 38, wherein the amino acid residue at position 18 is S, and the amino acid residue at position 2 is E, H, L, T, W or V; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide set forth in any of SEQ ID NO: 4, 5, 6, 7, 27-30, 39 and 41; or
a polypeptide consisting of SEQ ID NO: 38, wherein the amino acid residue at position 2 is T, and the amino acid residue at position 18 is N or S; and wherein the amino acid residue at position 17 of the N terminus of endostatin is S, A, L, I or T, and/or the amino acid residue at position 20 is S or T, and/or, the amino acid residue at position 21, if present, is S or T, and/or the amino acid residue at position 22, if present, is G, A, L, I or V; or
a polypeptide selected from amino acid sequences consisting of amino acid residue 1 to residue 39, 38, 37, 36, 34, 33, 32, 31, 29, 28, 27 or 26 of SEQ ID NO: 4, and amino acid sequences consisting of amino acid residue 1 to amino acid residue 39, 38, 37, 36, 35, 34, 33, 32, 31, 29, 28, 27, 26 or 25 of SEQ ID NO: 39; and
(2) a polynucleotide sequence complementary to any of the polynucleotide sequences of (1).

20. The expression vector of claim 19, wherein the polynucleotide sequence is selected from the group consisting of:
(1) a polynucleotide sequences encoding a polypeptide selected from the group consisting of:

```
                                              (SEQ ID NO: 52)
HTHRDFQPVLHLVALNSSLSGGMRGIRGAD;

(SEQ ID NO: 50)
Ac-HTHRDFQPVLHLVALNSSLSGGMRGIRGAD;
```

HTHRDFQPVLHLVALNSSLSGGMRGIRGAD-NH₂; (SEQ ID NO: 51)

Ac-HTHRDFQPVLHLVALNSSLSGGMRGIRGAD-NH₂; (SEQ ID NO: 6)

Ac-HTHRDFQPVLHLVALNSSLSGGMRG-NH₂; (SEQ ID NO: 7)

Ac-HTHRDFQPVLHLVALNSSLSGGMRGIRGADFQCFQ-NH₂; (SEQ ID NO: 5)

Ac-HTHRDFQPVLHLVALNSSLSGGMRGIRGADFQCFQQARAV-NH₂; (SEQ ID NO: 4)

HTHRDFQPVLHLVALNSNLSGGMRGIRGAD; (SEQ ID NO: 53)

Ac-HTHRDFQPVLHLVALNSNLSGGMRGIRGAD; (SEQ ID NO: 54)

HTHRDFQPVLHLVALNSNLSGGMRGIRGAD-NH₂; (SEQ ID NO: 55)

Ac-HTHRDFQPVLHLVALNSNLSGGMRGIRGAD-NH₂; (SEQ ID NO: 9)

Ac-HTHRDFQPVLHLVALNASLSGGMRGIRGAD-NH₂; (SEQ ID NO: 27)

Ac-HTHRDFQPVLHLVALNSSLTGGMRGIRGAD-NH₂; (SEQ ID NO: 28)

Ac-HTHRDFQPVLHLVALNASLTGGMRGIRGAD-NH₂; (SEQ ID NO: 29)

and

Ac-HTHRDFQPVLHLVALNSSLSGGMRGIRGA-NH₂; (SEQ ID NO: 41)

and (2) a sequence complementary to any of the polynucleotide sequences of (1).

* * * * *

SEQUENCE LISTING

<160> NUMBER OF SEQ ID NOS: 55

<210> SEQ ID NO 1
<211> LENGTH: 183
<212> TYPE: PRT
<213> ORGANISM: Homo sapiens

<400> SEQUENCE: 1

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 2
<211> LENGTH: 30
<212> TYPE: PRT
<213> ORGANISM: Artificial Sequence
<220> FEATURE:
<223> OTHER INFORMATION: Fragment of endostatin

<400> SEQUENCE: 2

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20                  25                  30

<210> SEQ ID NO 3
<211> LENGTH: 45
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (45)..(45)
<223> OTHER INFORMATION: Thr-NH2

<400> SEQUENCE: 3

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp Phe Gln
            20                  25                  30

Cys Phe Gln Gln Ala Arg Ala Val Gly Leu Ala Gly Thr
        35                  40                  45

<210> SEQ ID NO 4
<211> LENGTH: 40
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (40)..(40)
<223> OTHER INFORMATION: Val-NH2

<400> SEQUENCE: 4

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp Phe Gln
            20                  25                  30

Cys Phe Gln Gln Ala Arg Ala Val
        35                  40

<210> SEQ ID NO 5
<211> LENGTH: 35
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (35)..(35)
<223> OTHER INFORMATION: Gln-NH2

<400> SEQUENCE: 5

-continued

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp Phe Gln
            20                  25                  30

Cys Phe Gln
        35

<210> SEQ ID NO 6
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 6

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp
            20                  25                  30

<210> SEQ ID NO 7
<211> LENGTH: 25
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (25)..(25)
<223> OTHER INFORMATION: Gly-NH2

<400> SEQUENCE: 7

His Thr His Arg Asp Phe Gln Pro Val Leu His Leu Val Ala Leu Asn
1               5                   10                  15

Ser Ser Leu Ser Gly Gly Met Arg Gly
            20                  25

<210> SEQ ID NO 8
<211> LENGTH: 20
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (20)..(20)
<223> OTHER INFORMATION: Ser-NH2

<400> SEQUENCE: 8

His Thr His Arg Asp Phe Gln Pro Val Leu His Leu Val Ala Leu Asn
1               5                   10                  15

Ser Ser Leu Ser

```
<210> SEQ ID NO 9
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-His

<400> SEQUENCE: 9

His Thr His Arg Asp Phe Gln Pro Val Leu His Leu Val Ala Leu Asn
1               5                   10                  15

Ser Asn Leu Ser Gly Gly Met Arg Gly Ile Arg Gly Ala Asp
            20                  25                  30

<210> SEQ ID NO 10
<211> LENGTH: 192
<212> TYPE: PRT
<213> ORGANISM: Artificial Sequence
<220> FEATURE:
<223> OTHER INFORMATION: Recombinant human endostatin drug, endostar

<400> SEQUENCE: 10

Met Gly Gly Ser His His His His His Ser His Arg Asp Phe Gln
1               5                   10                  15

Pro Val Leu His Leu Val Ala Leu Asn Ala Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Glu Gly Pro Leu Lys Pro Gly Ala Arg Ile Phe Ser Phe
            100                 105                 110

Asp Gly Lys Asp Val Leu Arg His Pro Thr Trp Pro Gln Lys Ser Val
        115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190

<210> SEQ ID NO 11
<211> LENGTH: 30
<212> TYPE: PRT
<213> ORGANISM: Artificial Sequence
<220> FEATURE:
<223> OTHER INFORMATION: A mutant of a fragment from endostatin
```

```
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 11

His Thr His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 12

His Ala His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 13

His Glu His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
```

<223> OTHER INFORMATION: Asp-NH2

<400> SEQUENCE: 14

His Ser His Arg Asp Phe Gln Pro Val Leu His Leu Val Ala Ala Asn
1               5                   10                  15

Ser Pro Leu Ser Gly Gly Met Arg Gly Ile Arg Gly Ala Asp
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 15

His Ser His Arg Asp Phe Gln Pro Val Leu His Leu Val Ala Leu Ala
1               5                   10                  15

Ser Pro Leu Ser Gly Gly Met Arg Gly Ile Arg Gly Ala Asp
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 16

His Ser His Arg Asp Phe Gln Pro Val Leu His Leu Val Ala Leu Asn
1               5                   10                  15

Thr Pro Leu Ser Gly Gly Met Arg Gly Ile Arg Gly Ala Asp
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 17

His Ser His Arg Asp Phe Gln Pro Val Leu His Leu Val Ala Leu Asn
1               5                   10                  15

```
Ala Pro Leu Ser Gly Gly Met Arg Gly Ile Arg Gly Ala Asp
            20              25              30

<210> SEQ ID NO 18
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 18

His Ser His Arg Asp Phe Gln Pro Val Leu His Leu Val Ala Leu Asn
1               5                   10                  15

Ser Ala Leu Ser Gly Gly Met Arg Gly Ile Arg Gly Ala Asp
            20              25              30

<210> SEQ ID NO 19
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 19

His Ser His Arg Asp Phe Gln Pro Val Leu His Leu Val Ala Leu Asn
1               5                   10                  15

Ser Pro Ala Ser Gly Gly Met Arg Gly Ile Arg Gly Ala Asp
            20              25              30

<210> SEQ ID NO 20
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 20

His Ser His Arg Asp Phe Gln Pro Val Leu His Leu Val Ala Leu Asn
1               5                   10                  15

Ser Pro Leu Ala Gly Gly Met Arg Gly Ile Arg Gly Ala Asp
            20              25              30

<210> SEQ ID NO 21
<211> LENGTH: 30
<212> TYPE: PRT
```

```
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 21

His Ser His Arg Asp Phe Gln Pro Val Leu His Leu Val Ala Leu Asn
1               5                   10                  15

Ser Pro Leu Ser Ala Gly Met Arg Gly Ile Arg Gly Ala Asp
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 22

His Ser His Arg Asp Phe Gln Pro Val Leu His Leu Val Ala Leu Asn
1               5                   10                  15

Ser Pro Leu Ser Gly Ala Met Arg Gly Ile Arg Gly Ala Asp
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 23

His Ser His Arg Asp Phe Gln Pro Val Leu His Leu Val Ala Leu Asn
1               5                   10                  15

Ser Pro Leu Ser Gly Gly Met Arg Gly Asp Arg Gly Ala Asp
            20                  25                  30

<210> SEQ ID NO 24
<211> LENGTH: 17
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
```

```
<220> FEATURE:
<221> NAME/KEY: MISC_FEATURE
<222> LOCATION: (17)..(17)
<223> OTHER INFORMATION: Ser-NH2

<400> SEQUENCE: 24

His Thr His Arg Asp Phe Gln Pro Val Leu His Leu Val Ala Leu Asn
1               5                   10                  15

Ser

<210> SEQ ID NO 25
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 25

His Ser His Arg Asp Phe Gln Pro Val Leu His Leu Val Ala Leu Asn
1               5                   10                  15

Ser Ser Leu Ser Gly Gly Met Arg Gly Ile Arg Gly Ala Asp
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 26

His Ser His Arg Asp Phe Gln Pro Val Leu His Leu Val Ala Leu Asn
1               5                   10                  15

Ser Asn Leu Ser Gly Gly Met Arg Gly Ile Arg Gly Ala Asp
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 27

His Thr His Arg Asp Phe Gln Pro Val Leu His Leu Val Ala Leu Asn
```

```
                1               5                  10                  15
Ala Ser Leu Ser Gly Gly Met Arg Gly Ile Arg Gly Ala Asp
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 28

His Thr His Arg Asp Phe Gln Pro Val Leu His Leu Val Ala Leu Asn
1               5                  10                  15

Ser Ser Leu Thr Gly Gly Met Arg Gly Ile Arg Gly Ala Asp
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 29

His Thr His Arg Asp Phe Gln Pro Val Leu His Leu Val Ala Leu Asn
1               5                  10                  15

Ala Ser Leu Thr Gly Gly Met Arg Gly Ile Arg Gly Ala Asp
            20                  25                  30

<210> SEQ ID NO 30
<211> LENGTH: 549
<212> TYPE: DNA
<213> ORGANISM: Homo sapiens

<400> SEQUENCE: 30
cacagccacc gcgacttcca gccggtgctc cacctggttg cgctcaacag cccctgtca      60 ggcggcatgc ggggcatccg cggggccgac ttccagtgct ccagcaggc gcgggccgtg    120 gggctggcgg gcaccttccg cgccttcctg tcctcgcgcc tgcaggacct gtacagcatc    180
gtgcgccgtg ccgaccgcgc agccgtgccc atcgtcaacc tcaaggacga gctgctgttt    240
cccagctggg aggctctgtt ctcaggctct gagggtccgc tgaagcccgg ggcacgcatc    300
ttctcctttg acggcaagga cgtcctgagg caccccacct ggccccagaa gagcgtgtgg    360
catggctcgg accccaacgg cgcgcaggctg accgagagct actgtgagac gtggcggacg    420
gaggctccct cggccacggg ccaggcctcc tcgctgctgg ggggcaggct cctggggcag    480
agtgccgcga gctgccatca cgcctacatc gtgctctgca ttgagaacag cttcatgact    540
```

```
gcctccaag                                                              549
```

<210> SEQ ID NO 31
<211> LENGTH: 135
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 31

```
cacacccacc gcgacttcca gccggtgctc cacctggttg cgctcaacag cagcctgtca      60
ggcggcatgc ggggcatccg cggggccgac ttccagtgct ccagcaggc gcgggccgtg      120 gggctggcgg gcacc                                                      135
```

<210> SEQ ID NO 32
<211> LENGTH: 120
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 32

```
cacacccacc gcgacttcca gccggtgctc cacctggttg cgctcaacag cagcctgtca      60
ggcggcatgc ggggcatccg cggggccgac ttccagtgct ccagcaggc gcgggccgtg      120
```

<210> SEQ ID NO 33
<211> LENGTH: 105
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 33

```
cacacccacc gcgacttcca gccggtgctc cacctggttg cgctcaacag cagcctgtca      60
ggcggcatgc ggggcatccg cggggccgac ttccagtgct ccag                      105
```

<210> SEQ ID NO 34
<211> LENGTH: 90
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 34

```
cacacccacc gcgacttcca gccggtgctc cacctggttg cgctcaacag cagcctgtca      60
ggcggcatgc ggggcatccg cggggccgac                                       90
```

<210> SEQ ID NO 35
<211> LENGTH: 75
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 35

```
cacacccacc gcgacttcca gccggtgctc cacctggttg cgctcaacag cagcctgtca      60
ggcggcatgc ggggc                                                       75
```

```
<210> SEQ ID NO 36
<211> LENGTH: 60
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 36
cacacccacc gcgacttcca gccggtgctc cacctggttg cgctcaacag cagcctgtca      60

<210> SEQ ID NO 37
<211> LENGTH: 90
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 37
cacacccacc gcgacttcca gccggtgctc cacctggttg cgctcaacag caacctgtca      60
ggcggcatgc ggggcatccg cggggccgac                                       90

<210> SEQ ID NO 38
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is S, A, L, I, V or T
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is S or T
<220> FEATURE:
<221> NAME/KEY: MISC_FEATURE
<222> LOCATION: (21)..(21)
<223> OTHER INFORMATION: Xaa is G, A, L, I or V
<220> FEATURE:
<221> NAME/KEY: MISC_FEATURE
<222> LOCATION: (22)..(22)
<223> OTHER INFORMATION: Xaa is G, A, L, I or V
<220> FEATURE:
<221> NAME/KEY: MISC_FEATURE
<222> LOCATION: (30)..(30)
<223> OTHER INFORMATION: Asp-NH2

<400> SEQUENCE: 38

His Xaa His Arg Asp Phe Gln Pro Val Leu His Leu Val Ala Leu Asn
1               5                   10                  15

Xaa Xaa Leu Xaa Xaa Xaa Met Arg Gly Ile Arg Gly Ala Asp
            20                  25                  30

<210> SEQ ID NO 39
<211> LENGTH: 40
```

```
<212> TYPE: PRT
<213> ORGANISM: Artificial Sequence
<220> FEATURE:
<223> OTHER INFORMATION: A mutant of a fragment from endostatin

<400> SEQUENCE: 39

His Thr His Arg Asp Phe Gln Pro Val Leu His Leu Val Ala Leu Asn
1               5                   10                  15

Ser Asn Leu Ser Gly Gly Met Arg Gly Ile Arg Gly Ala Asp Phe Gln
            20                  25                  30

Cys Phe Gln Gln Ala Arg Ala Val
            35                  40

<210> SEQ ID NO 40
<211> LENGTH: 120
<212> TYPE: DNA
<213> ORGANISM: Artificial Sequence
<220> FEATURE:
<223> OTHER INFORMATION: Coding sequence of a mutant of a fragment from
      endostatin

<400> SEQUENCE: 40
cacacccacc gcgacttcca gccggtgctc cacctggttg cgctcaacag caacctgtca      60
ggcggcatgc ggggcatccg cggggccgac ttccagtgct ccagcaggc gcgggccgtg     120

<210> SEQ ID NO 41
<211> LENGTH: 29
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (29)..(29)
<223> OTHER INFORMATION: Ala-NH2

<400> SEQUENCE: 41

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala
            20                  25

<210> SEQ ID NO 42
<211> LENGTH: 5
<212> TYPE: PRT
<213> ORGANISM: Artificial Sequence
<220> FEATURE:
<223> OTHER INFORMATION: Tag sequence

<400> SEQUENCE: 42

Arg Arg Arg Arg Arg
1               5

<210> SEQ ID NO 43
<211> LENGTH: 6
<212> TYPE: PRT
<213> ORGANISM: Artificial Sequence
<220> FEATURE:
<223> OTHER INFORMATION: Tag sequence

<400> SEQUENCE: 43

His His His His His His
```

```
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: Tag sequence

<400> SEQUENCE: 44

Asp Tyr Lys Asp Asp Asp Asp Lys
1               5

<210> SEQ ID NO 45
<211> LENGTH: 8
<212> TYPE: PRT
<213> ORGANISM: Artificial Sequence
<220> FEATURE:
<223> OTHER INFORMATION: Tag sequence

<400> SEQUENCE: 45

Trp Ser His Pro Gln Phe Glu Lys
1               5

<210> SEQ ID NO 46
<211> LENGTH: 10
<212> TYPE: PRT
<213> ORGANISM: Artificial Sequence
<220> FEATURE:
<223> OTHER INFORMATION: Tag sequence

<400> SEQUENCE: 46

Trp Gln Lys Leu Ile Ser Glu Glu Asp Leu
1               5                   10

<210> SEQ ID NO 47
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Ac-His
<220> FEATURE:
<221> NAME/KEY: MISC_FEATURE
<222> LOCATION: (30)..(30)
<223> OTHER INFORMATION: Asp-NH2

<400> SEQUENCE: 47

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Ac-His

<400> SEQUENCE: 48
```

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20              25                  30

<210> SEQ ID NO 49
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (30)..(30)
<223> OTHER INFORMATION: Asp-NH2

<400> SEQUENCE: 49

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp
            20              25                  30

<210> SEQ ID NO 50
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Ac-His

<400> SEQUENCE: 50

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp
            20              25                  30

<210> SEQ ID NO 51
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (30)..(30)
<223> OTHER INFORMATION: Asp-NH2

<400> SEQUENCE: 51

His Thr His Arg Asp Phe Gln Pro Val Leu His Leu Val Ala Leu Asn
1               5                   10                  15

Ser Ser Leu Ser Gly Gly Met Arg Gly Ile Arg Gly Ala Asp
            20              25                  30

<210> SEQ ID NO 52
<211> LENGTH: 30
<212> TYPE: PRT
<213> ORGANISM: Artificial Sequence
<220> FEATURE:
<223> OTHER INFORMATION: synthetic

<400> SEQUENCE: 52

His Thr His Arg Asp Phe Gln Pro Val Leu His Leu Val Ala Leu Asn
1               5                   10                  15

```
Ser Ser Leu Ser Gly Gly Met Arg Gly Ile Arg Gly Ala Asp
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: A mutant of a fragment from endostatin

<400> SEQUENCE: 53

His Thr His Arg Asp Phe Gln Pro Val Leu His Leu Val Ala Leu Asn
1               5                   10                  15

Ser Asn Leu Ser Gly Gly Met Arg Gly Ile Arg Gly Ala Asp
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (1)..(1)
<223> OTHER INFORMATION: Ac-His

<400> SEQUENCE: 54

His Thr His Arg Asp Phe Gln Pro Val Leu His Leu Val Ala Leu Asn
1               5                   10                  15

Ser Asn Leu Ser Gly Gly Met Arg Gly Ile Arg Gly Ala Asp
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: A mutant of a fragment from endostatin
<220> FEATURE:
<221> NAME/KEY: MISC_FEATURE
<222> LOCATION: (30)..(30)
<223> OTHER INFORMATION: Asp-His

<400> SEQUENCE: 55

His Thr His Arg Asp Phe Gln Pro Val Leu His Leu Val Ala Leu Asn
1               5                   10                  15

Ser Asn Leu Ser Gly Gly Met Arg Gly Ile Arg Gly Ala Asp
            20                  25                  30
```